(12) United States Patent
Guo et al.

(10) Patent No.: US 10,858,421 B2
(45) Date of Patent: *Dec. 8, 2020

(54) INHIBITORS OF C5A FOR THE TREATMENT OF VIRAL PNEUMONIA

(71) Applicant: INFLARX GMBH, Jena (DE)

(72) Inventors: Renfeng Guo, Ann Arbor, MI (US); Niels Christoph Riedemann, Jeny (DE)

(73) Assignee: INFLARX GMBH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/256,100

(22) Filed: Jan. 24, 2019

(65) Prior Publication Data

US 2019/0202900 A1 Jul. 4, 2019

Related U.S. Application Data

(63) Continuation of application No. 15/127,676, filed as application No. PCT/EP2015/055947 on Mar. 20, 2015, now Pat. No. 10,227,397.

(30) Foreign Application Priority Data

Mar. 20, 2014 (EP) .................................... 14160947

(51) Int. Cl.
*A61K 39/00* (2006.01)
*C07K 16/18* (2006.01)
*C07K 14/47* (2006.01)

(52) U.S. Cl.
CPC ............ *C07K 16/18* (2013.01); *C07K 14/472* (2013.01); *A61K 2039/505* (2013.01); *C07K 2317/24* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 9,011,852 | B2 | 4/2015 | Rother et al. | |
| 10,227,397 | B2 | 3/2019 | Guo et al. | |
| 2012/0231008 | A1* | 9/2012 | Guo ...................... | C07K 16/18 424/139.1 |

FOREIGN PATENT DOCUMENTS

EP 2327725 A1 6/2011

OTHER PUBLICATIONS

Sun et al. Inhibition of Complement Activation Alleviates Acute Lung Injury Induced by Highly Pathogenic Avian nfluenza H5N1 Virus Infection. Am J Respir Cell Mol Biol vol. 49, Iss. 2, pp. 221-230, Aug. 2013.*
Tang et al. An overview of the recent outbreaks of the avian-origin influenza A (H7N9) virus in the human. Journal of he Chinese Medical Association 76 (2013) 245-248.*
Dondelinger et al. (2018) Understanding the Significance and Implications of Antibody Numbering and Antigen-Binding Surface/Residue Definition. Front. Immunol. 9:2278.*
Garcia et al. (2013) Complement C5 Activation during Influenza A Infection in Mice Contributes to Neutrophil Recruitment and Lung Injury. PLoS One 8(5): e64443.
Guo, Ren-Feng,et al., "Mediators and regulation of neutrophil accumulation in inflammatory responses in lung: insights from the IgG immune complex model 1,2 1. This article is part of a series of reviews on Reactive Oxygen and Nitrogen in Inflammationny," 2002, Free Radical Biology & Medicine, vol. 33, Nr: 3, pp. 303-310.
Lukacs, N.W. et al., "Complement-dependent immune complex-induced bronchial inflammation and hyperreactvity," Am J Physiol Lung Cell Mol Physiol, 280, L512-L518 (2001).
Mulligan M. S., et al., "Requirement and Role of C5a in Acute Lung Inflammatory Injury in Rats," 2013, Journal of Clinical Investigation, vol. 98, Nr 2, pp. 503-512.
Ohno et al. Antigen-binding specificities of antibodies are primarily determined by seven residues of VH. Proc. Nati. Acad. Sci. USA vol. 82, pp. 2945-2949, May 1985.
PCT Search Report and Written Opinion for PCT/EP2015/055947, completed May 27, 2015.
Rudikoff, S., et al., Single amino acid substitution altering antigen-binding specificity, Proc. Natl. Acad. Sci. 79(6): 1979-1983.
Sun et al. Inhibition of Complement Activation Alleviates Acute Lung Injury Induced by Highly Pathogenic Avian Influenza H5N1 Virus Infection. Am J Respir Cell Mol Biol vol. 49, Iss. 2, pp. 221-230, Aug. 2013.
Tang et al. An overview of the recent outbreaks of the avian-origin influenza A (H7N9) virus in the human. Journal of the Chinese Medical Association 76 (2013) 245-248.
Matthay, M.A., el al., "The acute respiratory distress syndrome," The Journal of Clinical Investigations 122, No. 8 2731-2740 (Aug. 2012).
Kojicic, M. et al. "Risk Factors for the Development of Acute Lung Injury in Patients With Infectious Pneumonia" Critical Care, 2012, 16: R46, 1-9.

* cited by examiner

Primary Examiner — Nianxiang Zou

(57) ABSTRACT

The present invention relates to inhibitors of C5a for use in the treatment of pneumonia, especially viral pneumonia. The invention also relates to the use of inhibitors of C5a in the preparation of a pharmaceutical composition for the treatment of pneumonia, especially viral pneumonia. The inventors further relates to methods for the treatment of pneumonia, especially viral pneumonia, comprising the step of administering a therapeutic amount of an inhibitor of C5a to a subject in need thereof.

13 Claims, 6 Drawing Sheets

Specification includes a Sequence Listing.

INHIBITORS OF C5A FOR THE TREATMENT OF VIRAL PNEUMONIA

CROSS-REFERENCE TO RELATED APPLICATIONS

This application is a Continuation of U.S. patent application Ser. No. 15/127,676, filed Sep. 20, 2016, which is a national stage application of International Application No. PCT/EP2015/055947, filed Mar. 20, 2015, which claims priority to European Patent Application 14160947.9, filed Mar. 20, 2014. The disclosures of each of which are hereby incorporated herein by reference in their entireties.

INCORPORATION BY REFERENCE OF MATERIAL SUBMITTED ELECTRONICALLY

Incorporated by reference in its entirety is a computer-readable amino acid/nucleotide sequence listing submitted concurrently herewith and identified as follows: One 8,749 byte ASCII (Text) file named "289734_ST25.txt" created on Jan. 24, 2019. The present invention relates to inhibitors of C5a for use in the treatment of pneumonia, especially viral pneumonia.

The invention also relates to the use of inhibitors of C5a in the preparation of a pharmaceutical composition for the treatment of pneumonia, especially viral pneumonia. The inventors further relates to methods for the treatment of pneumonia, especially viral pneumonia, comprising the step of administering a therapeutic amount of an inhibitor of C5a to a subject in need thereof.

BACKGROUND OF THE INVENTION

C5a

C5a is cleaved from C5 upon complement activation. Among the complement activation products, C5a is one of the most potent inflammatory peptides, with a broad spectrum of functions (Guo R F, and Ward P A. 2005. Annu. Rev. Immunol. 23:821-852). C5a is a glycoprotein present in the blood of healthy humans with a molecular weight of 11.2 kDa. The polypeptide portion of C5a contains 74 amino acids, accounting for a molecular weight of 8.2 kDa while the carbohydrate portion accounts for approximately 3 kDa. C5a exerts its effects through the high-affinity C5a receptors (C5aR and C5L2) (Ward P A. 2009. J. Mol. Med. 87(4): 375-378). C5aR belongs to the rhodopsin-type family of G-protein-coupled receptors with seven transmembrane segments; C5L2 is similar but is not G-protein-coupled. It is currently believed that C5a exerts its biological functions primarily through C5a-C5aR interaction, as few biological responses have been found for C5a-05L2 interaction. C5aR is widely expressed on myeloid cells including neutrophils, eosinophils, basophils, and monocytes, and non-myeloid cells in many organs, especially in the lung and liver, indicative of the importance of C5a/C5aR signaling. C5a has a variety of biological functions (Guo and Ward, 2005, supra). C5a is a strong chemoattractant for neutrophils and also has chemotactic activity for monocytes and macrophages. C5a causes an oxidative burst ($O_2$ consumption) in neutrophils and enhances phagocytosis and release of granular enzymes. C5a has also been found to be a vasodilator. C5a has been shown to be involved in modulation of cytokine expression from various cell types, to enhance expression of adhesion molecules on neutrophils. It is found that C5a becomes highly detrimental when it is overly produced in the disease settings, as it is a strong inducer and enhancer for inflammatory responses functioning in the up-stream of the inflammatory reaction chain. High doses of C5a can lead to nonspecific chemotactic "desensitization" for neutrophils, thereby causing broad dysfunction (Huber-Lang M et al. 2001. J. Immunol. 166(2):1193-1199).

C5a has been reported to exert numerous pro-inflammatory responses. For example, C5a stimulates the synthesis and release from human leukocytes of pro-inflammatory cytokines such as TNF-α, IL-1β, IL-6, IL-8, and macrophage migration inhibitory factor (MIF) (Hopken U et al. 1996. Eur J Immunol 26(5):1103-1109; Riedemann N C et al. 2004. J Immunol 173(2):1355-1359; Strieter R M et al. 1992. Am J Pathol 141(2):397-407). C5a produces a strong synergistic effect with LPS in production of TNF-α, macrophage inflammatory protein (MIP)-2, cytokine-induced neutrophil chemoattractant (CINC)-1, and IL-1β in alveolar epithelial cells (Riedemann N C et al. 2002. J. Immunol. 168(4):1919-1925; Rittirsch D et al. 2008. Nat Rev Immunol 8(10):776-787).

Blockade of C5a has also been proven to be protective in experimental models of sepsis and in many other models of inflammation such as ischemia/reperfusion injury, renal disease, graft rejection, malaria, rheumatoid arthritis, infectious bowel disease, inflammatory lung disease, lupus-like autoimmune diseases, neurodegenerative disease, etc. in various species as partially reviewed under Klos A. et al (Klos A. et al. 2009. Mol Immunol 46(14):2753-2766) and Allegretti M. et al (Allegretti M et al. 2005. Curr Med Chem 12(2):217-236). Moreover, it has been recently discovered that blockade of C5a has shown a strong therapeutic benefit in a tumor model in mice (Markiewski M M et al. 2008. Nat Immunol 9(11):1225-1235).

Avian Influenza

A novel avian influenza H7N9 virus emerged in China in February 2013 and a total of 139 patients with 45 fatal cases were confirmed till November 2013 (WHO. Human infection with avian influenza A(H7N9) virus—update. http://www.who.int/csr/don/2013_11_06/en/index.html (accessed on Nov. 16, 2013)). Most severe cases infected with H7N9 viral infection had manifestation of viral pneumonia with acute lung injury (ALI) and then progressed to severe respiratory failure and acute respiratory distress syndrome (ARDS) which was similar to the pathogenesis in patients infected with HPAI (highly pathogenic avian influenza) H5N1 virus or severe acute respiratory syndrome (SARS) virus (Beigel J H et al. 2005. N Engl J Med 353:1374-1385; Ip W K, et al. 2005. J Infect Dis 191:1697-1704). To date, no therapeutic strategies have been found to effectively treat these diseases. Accumulating studies suggested that the complement activation occurred in severe patients infected with influenza virus and was closely associated with the levels of proinflammatory mediators and lung injury. It has been reported that patients with severe pdmH1NI (pandemic influenza H1N1) virus infection had strong systemic complement activation with increased production of proinflammatory mediators (Berdal J E et al. 2011. J. Infect. 63(4):308-16; Ohta R et al. 2011. Microbiol. Immunol. 55(3):191-8). In addition, our previous studies have showed that the complement activation products in lung tissue sections and plasma samples were largely increased in the mouse model of H5N1 infection, and that the pathogenesis of ALI could be attributable, at least in part, to the complement activation and associated activation products such as C3a and C5a (Sun, S. et al. 2013. Am J Respir Cell Mol Biol 49: 221-230).

Complement system is a central part of the immune system in host defenses against pathogen invasion and in clearance of potentially damaging cell debris. However, excessive complement activation could be detrimental, since it may contribute to uncontrolled inflammatory responses and lead to tissue damages (Daniel Ricklin & John D Lambris. 2013 J Immunol 190(8):3831-8). Complement has become an interesting and promising target for treatment of various clinical diseases such as ischemia/reperfusion (I/R) injury, transplantation and autoimmune disorders (Lu F. et al. 2013. Cardiovasc. Pathol. 22:75-80; Tillou, X. et al. 2010. Kidney Int. 78:152-159; Manderson A P, et al. 2004. Annu Rev Immunol 22:431-456. Since the role of complement activation in the outcome of pathogen-induced diseases could be more complex due to the diversity of pathogen biological features including propagation and pathogenicity as well as a potential "dual role" of complement activation in the pathogen-driven immune responses, it is important to consider preservation of pathogen clearance function while inhibiting inflammation and tissue injury for the development of complement inhibitors for the treatment of pathogen-associated inflammatory disorders.

Complement activation product C5a exerts a predominant proinflammatory activity and mediates strong proinflammatory and modulatory signals in many disease models (Klos A. et al. 2009, supra). To date, many therapeutic compounds targeting C5a or C5aR such as C5a inhibitor C5aIP, C5aR antagonist PMX53 and CCX168 had been tested in the preclinical models with promising therapeutic benefits in transplantation, sepsis, arthritis, renal vasculitis and cancer (Woodruff, T. M. et al. 2011. Mol. Immunol. 48:1631-1642; Okada, N. et al. 2012. Clin. Exp. Pharmacol. 2:114; Tokodai, K. et al. 2010. Transplantation 90:1358-1365; Kohl, J. 2006. Curr. Opin. Mol. Ther. 8: 529-538). It was also demonstrated that antibody blockade of C5a or C5a receptor abrogated the excessive immune responses in the mouse model of *Plasmodium berghei* ANKA (PbA) infection (Patel, S. N. et al. 2008. J. Exp. Med. 205:1133-1143). Similarly, our previous study employing a mouse model of HPAI H5N1 viral pneumonia revealed that anti-C5a treatment significantly attenuated lung injury and improved the survival rate (Sun, S. et al. 2013, supra). Since membrane attack complex (MAC) plays an essential role in the innate host defenses again invading pathogens, it appears to be advantageous to apply C5a blockade strategy inhibiting the inflammatory responses derived from pathogen infection while leaving the arm of MAC formation intact.

Technical Problems Underlying the Present Invention

One of the problems underlying the invention was the provision of therapeutic approaches for the treatment of viral pneumonia, in particular for the treatment of viral pneumonia caused by the novel avian influenza H7N9 virus.

So far it has not been studied whether an anti-C5a treatment would be effective in the treatment of viral pneumonia caused by the novel avian influenza virus H7N9. Previous studies are focused on other avian influenza viruses (H5N1; cf. Sun, S. et al. 2013, supra) and only employed a mouse model to study viral pneumonia caused by the avian influenza virus. Positive results from a mouse model might not always be transferable to an actual treatment of human patients.

The inventors of the instant application have applied IFX-1, a highly potent neutralizing mAb against human C5a, which is currently in the clinical development, in a monkey model of H7N9 virus infection to explore the therapeutic potential of complement inhibition in the treatment of H7N9 virus-induced severe pneumonia. To our knowledge, this is the first time that an anti-C5a treatment of viral pneumonia has been studied in a monkey model.

The data in the experimental section shown below demonstrate that excessive complement activation occurs in the H7N9 infection and it is attributable to the development of ALI (acute lung injury) and systemic inflammation.

The present inventors have found that anti-C5a treatment in H7N9 infected monkeys substantially attenuated ALI and led to strongly reduced lung histopathologic injury scores as well as decreased lung infiltration of macrophages and neutrophils when compared to untreated infected African green monkeys. In addition, the intensity of the infectious SIRS (systemic inflammatory response syndrome) caused by H7N9 was markedly reduced by IFX-1 treatment, as evidenced by a significant reduction in body temperature increases and in plasma levels of inflammatory mediators. The virus titers in the infected lungs of AGMs were unexpectedly diminished by IFX-1 treatment. This is very surprising, since there is no known mechanism which would suggest an involvement of C5a in virus replication.

The results suggest that complement inhibition is a highly promising strategy for an adjunctive treatment of severe viral pneumonia. The therapeutic effects associated with the administration of a C5a inhibitor are so preeminent that even a monotherapy for viral pneumonia based on a C5a inhibitor appears to be feasible.

The above overview does not necessarily describe all advantages associated with and problems solved by the present invention.

SUMMARY OF THE INVENTION

In a first aspect the present invention relates to an inhibitor of C5a for use in the reduction of viral load and/or reduction of acute lung injury (ALI) in a subject suffering from viral pneumonia.

In a second aspect the present invention relates to an inhibitor of C5a for use in the treatment of pneumonia (preferably viral pneumonia) in a subject, wherein the inhibitor is for use as a monotherapy.

In a third aspect the present invention relates to an inhibitor of C5a for use in the treatment of viral pneumonia in a subject, wherein the viral pneumonia in the subject is caused by an H7N9 virus.

In a fourth aspect the present invention relates to an inhibitor of C5a for use in the treatment of pneumonia (preferably viral pneumonia) in a subject, wherein the subject is a primate, preferably an ape, more preferably a human.

This summary of the invention does not necessarily describe all features of the invention.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

As used herein, "human C5a" refers to the following 74 amino acid peptide:

```
                                              (SEQ ID NO: 1)
TLQKKIEEIA AKYKHSVVKK CCYDGACVNN DETCEQRAAR

ISLGPRCIKA FTECCVVASQ LRANISHKDM QLGR.
```

As used herein, the term "human C5a" refers to glycosylated forms and to deglycosylated forms of this 74 amino acid peptide. The terms "human C5a" and "hC5a" are used interchangeably herein.

The term "inhibitor of C5a", as used herein, refers to a compound that inhibits a biological activity of C5a. The term "inhibitor of C5a" particularly refers to a compound that interferes with the binding of C5a to the C5a receptors, C5aR and C5L2; especially to a compound that interferes with the binding of C5a to C5aR. Accordingly, the term "inhibitor of C5a" encompasses compounds that specifically bind to C5a and inhibit binding of C5a to C5aR as well as compounds that specifically bind to C5aR and inhibit binding of C5a to C5aR. Exemplary inhibitors of C5a include the C5a inhibitory peptide (C5aIP), the selective C5a receptor antagonists PMX53 and CCX168, and the anti-C5a antibodies disclosed in WO 2011/063980 A1 (also published as US 2012/0231008 A1). The term "inhibitor of C5a" and "C5a inhibitor" are used interchangeably herein.

The term "binding moiety", as used herein, refers to any molecule or part of a molecule that can specifically bind to a target molecule or target epitope. Preferred binding moieties in the context of the present application are (a) antibodies or antigen-binding fragments thereof; (b) oligonucleotides; (c) antibody-like proteins; or (d) peptidomimetics. Exemplary "binding moieties" that are especially well-suited for practicing the present invention are capable of binding to a conformational epitope of human C5a which is formed by the two amino acid sequences NDETCEQRA (SEQ ID NO: 2) and SHKDMQL (SEQ ID NO: 3). Further exemplary "binding moieties" that are especially well-suited for practicing the present invention are capable of binding to a conformational epitope of human C5a which is formed by the two amino acid sequences DETCEQR (SEQ ID NO: 4) and HKDMQ (SEQ ID NO: 5).

As used herein, a first compound (e.g. an antibody) is considered to "bind" to a second compound (e.g. an antigen, such as a target protein), if it has a dissociation constant $K_d$ to said second compound of 1 mM or less, preferably 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant ($K_d$) which is lower than the dissociation constant for the second target. Preferably the dissociation constant ($K_d$) for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding moiety does not bind specifically.

As used herein, the term "$K_d$" (usually measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof). In the context of the present application, the "$K_d$" value is determined by surface plasmon resonance spectroscopy (Biacore™) at room temperature (25° C.).

An "epitope", also known as antigenic determinant, is the part of a macromolecule that is recognized by the immune system, specifically by antibodies, B cells, or T cells. As used herein, an "epitope" is the part of a macromolecule capable of binding to a binding moiety (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which a binding moiety of the invention (e.g. an antibody or an antigen-binding fragment thereof) binds simultaneously, wherein these at least two separate regions are interrupted by one or more regions in the primary sequence to which a binding moiety of the invention does not bind. Preferably, such a "conformational epitope" is present on a polypeptide, and the two separate regions in the primary sequence are two separate amino acid sequences to which a binding moiety of the invention (e.g. an antibody or an antigen-binding fragment thereof) binds, wherein these at least two separate amino acid sequences are interrupted by one or more amino acid sequences in the primary sequence to which a binding moiety of the invention does not bind. Preferably, the interrupting amino acid sequence is a contiguous amino acid sequence comprising two or more amino acids to which the binding moiety does not bind. The at least two separate amino acid sequences to which a binding moiety of the invention binds are not particularly limited with regard to their length. Such a separate amino acid sequence may consists of only one amino acid as long as the total number of amino acids within said at least two separate amino acid sequences is sufficiently large to effect specific binding between the binding moiety and the conformational epitope.

A "paratope" is the part of an antibody that binds to the epitope. In the context of the present invention, a "paratope" is the part of a binding moiety (e.g. an antibody or antigen-binding fragment thereof) as described herein that binds to the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, antibodies expressed in eukaryotes (e.g. CHO cells), glycosylated antibodies, and any antigen-binding antibody fragments and derivatives as described below. Each heavy chain is comprised of a heavy chain variable region (abbreviated herein as VH or $V_H$) and a heavy chain constant region (abbreviated herein as CH or $C_H$). The heavy chain constant region can be further subdivided into three parts, referred to as CH1, CH2, and CH3 (or $C_H1$, $C_H2$, and $C_H3$). Each light chain is comprised of a light chain variable region (abbreviated herein as VL or $V_L$) and a light chain constant region (abbreviated herein as CL or $C_L$). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those skilled in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1 (Heap C. J. et al. (2005) *Analysis of a 17-amino acid residue, virus-neutralizing microantibody*. J. Gen. Virol. 86:1791-1800). Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007 (Qiu X.-Q. et al. (2007) *Small antibody mimetics comprising two complementary-determining regions and a framework region for tumor targeting*. Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope, e.g. to the conformational epitope of human C5a formed by the amino acid sequences according to SEQ ID NO: 2 and SEQ ID NO: 3; or the conformational epitope of human C5a formed by the amino acid sequences DETCEQR (SEQ ID NO: 4) and HKDMQ (SEQ ID NO: 5). The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgA1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover, antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response in a human subject when the antibodies are injected than would the constant region from a non-human source. However, the definition is not limited to this particular example.

The term "humanized antibody" refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, Frontiers in Bioscience, 13:1619-1633, the content of which is herein incorporated by reference in its entirety. The review article by Almagro & Fransson is briefly summarized in US 2012/0231008 A1 which is the national stage entry of international patent application WO 2011/063980 A1. The contents of US 2012/0231008 A1 and WO 2011/063980 A1 are herein incorporated by reference in their entirety.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulins and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A.

90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody" as used herein, is intended to refer to an antibody which is substantially free of other antibodies having different antigenic specificities (e.g., an isolated antibody that specifically binds to C5a is substantially free of antibodies that specifically bind antigens other than C5a). An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. In one embodiment of the invention, a combination of "isolated" monoclonal antibodies relates to antibodies having different specificities and being combined in a well-defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E. N. and Gold L. (2000), Aptamers as therapeutic and diagnostic agents. J. Biotechnol. 74(1):5-13). The nucleic acid aptamer may be a DNA or RNA molecule. The aptamers may contain modifications, e.g. modified nucleotides such as 2'-fluorine-substituted pyrimidines.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop is typically between 10 and 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from nonimmunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of nonnatural amino acids).

"Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (iii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

As used herein, the expression "comprises 1, 2, or 3 amino acid exchanges, preferably conservative amino acid exchanges, 1, 2, or 3 amino acid deletions, and/or 1, 2, or 3 amino acid additions" has to be understood in that the so modified amino acid sequence contains no more than 3 amino acid exchanges (preferably conservative amino acid exchanges), no more than 3 amino acid deletions, and no more than 3 amino acid additions. Consequently, the thus characterized amino acid sequence has a maximum of 9 amino acid modifications (3 exchanges+3 deletions+3 additions). Accordingly, the afore-mentioned expression is a closed expression, even though the term "comprises" is understood as an open expression in other contexts.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. Regarding variants and derivatives of a polypeptide, it is not required that the variant or derivative exhibits such an activity to the same extent as the parent polypeptide. A variant is regarded as a variant within the context of the present application, if it exhibits the relevant activity to a degree of at least 10% (e.g. at least 20%, at least 30%, at least 40%, or at least 50%) of the activity of the parent polypeptide. Likewise, a derivative is regarded as a derivative within the context of the present application, if it exhibits the relevant biological activity to a degree of at least 10% of the activity of the parent polypeptide. A particularly relevant "biological activity" in the context of the present invention is a binding activity to the conformational epitope of human C5a formed by the amino acid sequences according to SEQ ID NO: 2 and SEQ ID NO: 3. Preferably, the relevant "biological activity" in the context of the present invention is a binding activity to the conformational epitope of human C5a formed by the amino acid sequences DETCEQR (SEQ ID NO: 4) and KDM. Assays for determining binding activity are known to a person of ordinary skill in the art and include ELISA and surface plasmon resonance assays.

As used herein, a "patient" means any mammal or bird who may benefit from a treatment with an inhibitor of C5a described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including monkeys (e.g. African green monkeys, chimpanzees, bonobos, gorillas) and human beings. It is particularly preferred that the "patient" is a human being. The terms "patient" and "subject to be treated" (or just: "subject") are used interchangeably herein.

As used herein, the term "monkey" refers to any non-human primate mammal, if the context does not say otherwise. For example, in the section "Examples" below, the term "monkey" is typically used as an abbreviation for "African green monkey".

As used herein, the term "ape" refers to Old World anthropoid mammals belonging to the biological superfamily Hominoidea and, accordingly, includes gibbons (family Hilobatidae), orang-utans (genus *Pongo*), gorillas (genus *Gorilla*), chimpanzees (genus *Pan*), and humans (genus *Homo*).

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in a subject for a certain amount of time. For example, if an inhibitor of C5a described herein (e.g. an anti-C5a antibody or an antigen-binding fragment thereof) is administered to a subject with the aim of preventing a disease or disorder, said disease or disorder is prevented from occurring at least on the day of administration and preferably also on one or more days (e.g. on 1 to 30 days; or on 2 to 28 days; or on 3 to 21 days; or on 4 to 14 days; or on 5 to 10 days) following the day of administration.

As used herein, "administering" includes in vivo administration, as well as administration directly to tissue ex vivo, such as vein grafts.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

An "effective amount" is an amount of a therapeutic agent sufficient to achieve the intended purpose. The effective amount of a given therapeutic agent will vary with factors such as the nature of the agent, the route of administration, the size and species of the subject to receive the therapeutic agent, and the purpose of the administration. The effective amount in each individual case may be determined empirically by a skilled artisan according to established methods in the art.

As used herein, the term "adjunctive therapy" refers to a combination therapy, in which at least two different drugs are administered to the patient. These at least two different drugs can be formulated into one single pharmaceutical composition containing both drugs. Alternatively, each drug can be formulated into a separate pharmaceutical composition and the pharmaceutical compositions are separately administered (e.g. at different time-points and/or by different routes of administration) to the patient. In this latter alternative, the (at least) two different drugs can be present in a kit-of-parts. The present disclosure particularly features a therapy with a C5a inhibitor as an adjunctive therapy to antiviral treatment with an antiviral agent.

As used herein, the term "antiviral agent" includes without limitation: neuraminidase inhibitors (e.g. orally inhaled zanamivir or oral oseltamivir) and virus-specific antibodies.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. Eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (D. Hu et al., Curr. Opin. Biotechnol. 8:148-153, 1997); "Serum free Media" (K. Kitano, Biotechnol. 17:73-106, 1991); and "Suspension Culture of Mammalian Cells" (J. R. Birch et al. Bioprocess Technol. 10:251-270, 1990).

EMBODIMENTS OF THE INVENTION

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to an inhibitor of C5a for use in the reduction of viral load and/or reduction of acute lung injury (ALI) in a subject suffering from viral pneumonia, especially HxNx-mediated viral pneumonia.

In an alternative wording, the first aspect of the present invention is directed to the use of an inhibitor of C5a in the preparation of a pharmaceutical composition for the reduction of viral load and/or reduction of acute lung injury (ALI) in a subject suffering from viral pneumonia, especially HxNx-mediated viral pneumonia.

In another alternative wording, the first aspect of the present invention is directed to a method for the reduction of viral load and/or reduction of acute lung injury (ALI) in a subject suffering from viral pneumonia, especially HxNx-mediated viral pneumonia, said method comprising the step of administering a therapeutic amount of an inhibitor of C5a to said subject.

In a second aspect the present invention is directed to an inhibitor of C5a for use in the treatment of pneumonia (preferably viral pneumonia, especially HxNx-mediated viral pneumonia) in a subject, wherein the inhibitor is for use as a monotherapy.

In an alternative wording, the second aspect of the present invention is directed to the use of an inhibitor of C5a in the preparation of a pharmaceutical composition for the treatment of pneumonia (preferably viral pneumonia, especially HxNx-mediated viral pneumonia) in a subject, wherein the pharmaceutical composition is to be used as a monotherapy.

In another alternative wording, the second aspect of the present invention is directed to a method for the treatment of pneumonia (preferably viral pneumonia, especially HxNx-mediated viral pneumonia), said method comprising the step of administering a therapeutic amount of an inhibitor of C5a to a subject in need thereof, wherein the inhibitor is administered as a monotherapy.

In a third aspect the present invention is directed to an inhibitor of C5a for use in the treatment of viral pneumonia in a subject, wherein the viral pneumonia in the subject is caused by an H7N9 virus.

In an alternative wording, the third aspect of the present invention is directed to the use of an inhibitor of C5a in the preparation of a pharmaceutical composition for the treatment of viral pneumonia in a subject, wherein the viral pneumonia in the subject is caused by an H7N9 virus.

In another alternative wording, the third aspect of the present invention is directed to a method for the treatment of viral pneumonia, said method comprising the step of administering a therapeutic amount of an inhibitor of C5a to a subject in need thereof, wherein the viral pneumonia in said subject is caused by an H7N9 virus.

In a fourth aspect the present invention is directed to an inhibitor of C5a for use in the treatment of pneumonia (preferably viral pneumonia, especially HxNx-mediated viral pneumonia) in a subject, wherein the subject is a primate, preferably an ape, more preferably a human.

In an alternative wording, the fourth aspect of the present invention is directed to the use of an inhibitor of C5a in the preparation of a pharmaceutical composition for the treatment of pneumonia (preferably viral pneumonia, especially HxNx-mediated viral pneumonia) in a subject, wherein the subject is a primate, preferably an ape, more preferably a human.

In another alternative wording, the fourth aspect of the present invention is directed to a method for the treatment of pneumonia (preferably viral pneumonia, especially HxNx-mediated viral pneumonia), said method comprising the step of administering a therapeutic amount of an inhibitor of C5a to a subject in need thereof, wherein said subject is a primate, preferably an ape, more preferably a human.

In one embodiment of the second, third, or fourth aspect of the invention, the inhibitor of C5a is for use in the reduction of viral load and/or acute lung injury (ALI) in a subject suffering from viral pneumonia or—in an alternative wording—the pharmaceutical composition is for the reduction of viral load and/or reduction of acute lung injury (ALI) in a subject suffering from viral pneumonia or—in another alternative wording—the method is for reduction of viral load and/or acute lung injury (ALI) in a subject suffering from viral pneumonia.

In one embodiment of the first, third, or fourth aspect of the invention, the inhibitor of C5a is for use as a monotherapy or—in an alternative wording—the pharmaceutical composition is to be used as a monotherapy or—in another alternative wording—the inhibitor of C5a is administered as a monotherapy.

In another embodiment of the first, third or fourth aspect of the invention, the inhibitor of C5a is for use in an adjunctive therapy with an antiviral agent or—in an alternative wording—the pharmaceutical composition is to be used in an adjunctive therapy with an antiviral agent or—in another alternative wording—the method additionally comprises the step of administering a therapeutic amount of an antiviral agent to said subject. Antiviral agents suitable for use in such an adjunctive therapy include without limitation: neuraminidase inhibitors (e.g. orally inhaled zanamivir or oral oseltamivir) and virus-specific antibodies.

In one embodiment of the first, second, or fourth aspect of the invention, the pneumonia in the subject is caused by an HxNx virus. In some embodiments, the HxNx virus is selected from the group consisting of H1N1, H1N3, H2N2, H3N2, H5N1, H7N2, H7N3, H7N7, H7N9, H9N2, H10N7, and H10N8. In particular embodiments of the first, second, or fourth aspect of the invention, the HxNx virus is H7N9.

In one embodiment of the first, second, or third aspect of the invention, the subject is a primate, preferably an ape, more preferably a human.

The present invention further provides combinations of the four aspects defined above. For example, in one embodiment, the features of the first, second, and third aspect of the invention can be combined. In another embodiment, the features of the first, second, and fourth aspect of the invention can be combined. In another embodiment, the features of the first, third, and fourth aspect of the invention can be combined. In another embodiment, the features of the second, third, and fourth aspect of the invention can be combined. In yet another embodiment, the features of the first, second, third, and fourth aspect of the invention can be combined.

In one embodiment of the first, second, third, or fourth aspect of the invention, the inhibitor of C5a is selected from the group consisting of (i) compounds (binding moieties) that specifically bind to C5a and inhibit binding of C5a to C5aR; and (ii) compounds (binding moieties) that specifically bind to C5aR and inhibit binding of C5a to C5aR. Exemplary compounds that specifically bind to C5a include the C5a inhibitory peptide (C5aIP) and anti-C5a antibodies, such as the anti-C5a antibodies disclosed in WO 2011/063980 A1 (also published as US 2012/0231008 A1). Exemplary compounds that specifically bind to C5aR include the selective C5a receptor antagonists PMX53 and CCX168.

In one embodiment of the first, second, third, or fourth aspect of the invention, the inhibitor of C5a is a binding moiety specifically binding to human C5a. In a further embodiment, said binding moiety is selected from the group consisting of
(a) antibodies or antigen-binding fragments thereof;
(b) oligonucleotides;
(c) antibody-like proteins; and
(d) peptidomimetics.

In one embodiment of the first, second, third, or fourth aspect of the invention, the binding moiety specifically binds to a conformational epitope formed by amino acid sequences NDETCEQRA (SEQ ID NO: 2) and SHKDMQL (SEQ ID NO: 3) of human C5a. Binding to the conformational formed by the amino acid sequences according to SEQ ID NOs: 2 and 3 means that the binding moiety binds to at least one amino acid within the amino acid sequence according to SEQ ID NO: 2 and to at least one amino acid within the amino acid sequence according to SEQ ID NO: 3. SEQ ID NO: 2 corresponds to amino acids 30-38 of human C5a. SEQ ID NO: 3 corresponds to amino acids 66-72 of human C5a.

In preferred embodiments of the first, second, third, or fourth aspect of the invention, the binding moiety binds to at least one amino acid within the amino acid sequence according to DETCEQR (SEQ ID NO: 4). SEQ ID NO: 4 corresponds to amino acids 31-37 of human C5a.

In further preferred embodiments of the first, second, third, or fourth aspect of the invention, the binding moiety binds to at least one amino acid within the amino acid sequence according to HKDMQ (SEQ ID NO: 5), more preferably to at least one amino acid within the amino acid sequence KDM. SEQ ID NO: 5 corresponds to amino acids 67-71 of human C5a; the sequence KDM corresponds to amino acids 68-70 of human C5a.

In preferred embodiments of the first, second, third, or fourth aspect of the invention, the binding moiety binds to at least one amino acid within the amino acid sequence DETCEQR (SEQ ID NO: 4) and to at least one amino acid within the amino acid sequence HKDMQ (SEQ ID NO: 5).

In particularly preferred embodiments of the first, second, third, or fourth aspect of the invention, the binding moiety binds to at least one amino acid within the amino acid sequence DETCEQR (SEQ ID NO: 4) and to at least one amino acid within the amino acid sequence KDM.

In preferred embodiments of the first, second, third, or fourth aspect of the invention, the two sequences forming the conformational epitope (e.g. sequence pairs according to SEQ ID NO: 2 and 3; SEQ ID NO: 4 and 5; or SEQ ID NO: 4 and sequence KDM) are separated by 1-50 contiguous amino acids that do not participate in binding to the binding moiety of the invention. In the following, such amino acids that do not participate in binding to the binding moiety of the invention will be referred to as "non-binding amino acids". The two sequences forming the conformational epitope are preferably separated by 6-45 contiguous non-binding amino acids, more preferably by 12-40 contiguous non-binding amino acids, more preferably by 18-35 contiguous non-binding amino acids, more preferably by 24-30 contiguous non-binding amino acids, more preferably by 25-29 contiguous non-binding amino acids, even more preferably by 26-28 contiguous non-binding amino acids, and most preferably by 27 contiguous non-binding amino acids.

In preferred embodiments of the first, second, third, or fourth aspect of the invention, the binding moiety has a binding constant to human C5a with a $K_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less.

In preferred embodiments of the first, second, third, or fourth aspect of the invention, the dissociation constant $K_d$ between the binding moiety and human C5a is between 1 pM (picomolar) and 5 nM (nanomolar), more preferably between 2 pM and 4 nM, more preferably between 5 pM and 3 nM, more preferably between 10 pM and 2 nM, more preferably between 50 pM and 1 nM, more preferably between 100 pM and 900 pM, more preferably between 200 pM and 800 pM, more preferably between 300 pM and 700 pM, and even more preferably between 400 pM and 600 pM.

In preferred embodiments of the first, second, third, or fourth aspect of the invention, one binding moiety exhibits at least 75% blocking activity, preferably at least 80% blocking activity, more preferably at least 85% blocking activity, more preferably at least 90% blocking activity, more preferably at least 95% blocking activity for biological effects induced by one molecule C5a, particularly human C5a. These preferred blocking activities refer to those embodiments, wherein the binding moiety comprises a single paratope binding to C5a, preferably human C5a. In embodiments, wherein the binding moiety comprises two or more C5a-specific paratopes, said blocking activities of at least 75%, preferably at least 80%, more preferably at least 85%, etc. are achieved when one binding-moiety molecule is contacted with a number of C5a molecules equal to the number of C5a-specific paratopes present in the binding moiety. In other words, when the paratopes of a binding moiety described herein and C5a are present in equimolar concentrations, the binding moiety exhibits at least 75% blocking activity, preferably at least 80% blocking activity, more preferably at least 85% blocking activity, more preferably at least 90% blocking activity, and more preferably at least 95% blocking activity for biological effects induced by C5a. A preferred biological effect to be blocked is C5a-induced lysozyme release from human whole blood cells. Assays for determining this C5a-induced lysozyme release and its blocking are described, for example, in WO 2011/063980 A1.

In preferred embodiments of the first, second, third, or fourth aspect of the invention, the binding moiety does not inhibit CH50 activity in human plasma. Assays for determining CH50 activity are known to the skilled person and are described, for example, in WO 2011/063980 A1.

In preferred embodiments of the first, second, third, or fourth aspect of the invention, the binding moiety does not exhibit a blocking activity on at least one C5b-induced biological effect; preferably the binding moiety does not exhibit a blocking activity on any C5b-induced biological effect.

In preferred embodiments of the first, second, third, or fourth aspect of the invention, the binding moiety is capable of reducing E. coli induced IL-8 production in human whole blood. Assays for measuring IL-8 production in whole blood are known to the skilled person and are described, for example, in WO 2011/063980 A1.

In preferred embodiments of the first, second, third, or fourth aspect of the invention, the binding moiety is an antibody, said antibody being selected from the group consisting of polyclonal antibodies, monoclonal antibodies, monovalent antibodies, bispecific antibodies, heteroconjugate antibodies, multispecific antibodies, deimmunized antibodies, chimeric antibodies, humanized (in particular CDR-grafted) antibodies, and human antibodies.

In preferred embodiments of the first, second, third, or fourth aspect of the invention, the binding moiety is an antigen-binding fragment of an antibody, said fragment being selected from the group consisting of Fab fragments, Fab' fragments, F(ab')$_2$ fragments, Fd fragments, Fv fragments, disulfide-linked Fvs (dsFv), single domain antibodies (also known as nanobodies), and single chain Fv (scFv) antibodies.

In one embodiment of the first, second, third or fourth aspect of the invention, the binding moiety is an antibody or an antigen-binding fragment thereof, wherein said antibody or antigen-binding fragment thereof comprises
(i) a heavy chain CDR3 sequence as set forth in SEQ ID NO: 6; or
(ii) a heavy chain CDR3 sequence as set forth in SEQ ID NO: 7;
wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In one embodiment of the first, second, third or fourth aspect of the invention, the binding moiety is an antibody or an antigen-binding fragment thereof, wherein said antibody or antigen-binding fragment thereof comprises
(iii) a light chain CDR3 sequence as set forth in SEQ ID NO: 8; or
(iv) a light chain CDR3 sequence as set forth in SEQ ID NO: 9;
wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of the first, second, third or fourth aspect of the invention, the binding moiety is an antibody or an antigen-binding fragment thereof, wherein said antibody or antigen-binding fragment thereof comprises a heavy chain CDR3 sequence as set forth in SEQ ID NO: 6 and a light chain CDR3 sequence as set forth in SEQ ID NO: 8; or
(ii) a heavy chain CDR3 sequence as set forth in SEQ ID NO: 7 and a light chain CDR3 sequence as set forth in SEQ ID NO: 9;
wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions; and
wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In one embodiment of the first, second, third or fourth aspect of the invention, the binding moiety is an antibody or an antigen-binding fragment thereof, wherein said antibody or antigen-binding fragment thereof comprises at least one of the following sequences:
(v) a heavy chain CDR2 sequence according to SEQ ID NO: 10;
(vi) a heavy chain CDR2 sequence according to SEQ ID NO: 11;
(vii) a light chain CDR2 sequence according to SEQ ID NO: 12;
(viii) a light chain CDR2 sequence according to SEQ ID NO: 13;
(ix) a heavy chain CDR1 sequence according to SEQ ID NO: 14;
(x) a heavy chain CDR1 sequence according to SEQ ID NO: 15;
(xi) a light chain CDR1 sequence according to SEQ ID NO: 16; or
(xii) a light chain CDR1 sequence according to SEQ ID NO: 17;
wherein the heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein the light chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein the heavy chain CDR1 sequence optionally comprises 1, 2 or 3 amino acid exchanges, preferably conservative amino acid exchanges, 1, 2, or 3 amino acid deletions, and/or 1, 2, or 3 amino acid additions; and
wherein the light chain CDR1 sequence optionally comprises 1, 2, or 3 amino acid exchanges, preferably conservative amino acid exchanges, 1, 2, or 3 amino acid deletions, and/or 1, 2, or 3 amino acid additions.

Preferably, the total number of these optional changes recited above in each one of the amino acid sequences according to SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, and SEQ ID NO: 17, i.e. the total number of exchanges, deletions and additions in each sequence, is 1 or 2.

Preferably the total number of exchanges, deletions, and additions added up for all CDRs present in an antibody or antigen-binding fragment thereof is between 1 and 5 (e.g. 1, 2, 3, 4, or 5).

In preferred embodiments of the first, second, third or fourth aspect of the invention, the antibody or antigen-binding fragment thereof comprises one of the sets of heavy chain CDR3, heavy chain CDR2, and heavy chain CDR1 sequences as listed below in Table 1,
wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each heavy chain CDR1 sequence optionally comprises 1, 2, or 3 amino acid exchanges, preferably conservative amino acid exchanges, 1, 2, or 3 amino acid deletions, and/or 1, 2, or 3 amino acid additions:

TABLE 1

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| A | SEQ ID NO: 6 | SEQ ID NO: 10 | SEQ ID NO: 14 |
| B | SEQ ID NO: 6 | SEQ ID NO: 10 | SEQ ID NO: 15 |
| C | SEQ ID NO: 6 | SEQ ID NO: 11 | SEQ ID NO: 14 |
| D | SEQ ID NO: 6 | SEQ ID NO: 11 | SEQ ID NO: 15 |
| E | SEQ ID NO: 7 | SEQ ID NO: 10 | SEQ ID NO: 14 |
| F | SEQ ID NO: 7 | SEQ ID NO: 10 | SEQ ID NO: 15 |
| G | SEQ ID NO: 7 | SEQ ID NO: 11 | SEQ ID NO: 14 |
| H | SEQ ID NO: 7 | SEQ ID NO: 11 | SEQ ID NO: 15 |

In preferred embodiments of the first, second, third or fourth aspect of the invention, the antibody or antigen-binding fragment thereof comprises one of the following sets of light chain CDR3, light chain CDR2, and light chain CDR1 sequences as listed in Table 2,
wherein each light chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each light chain CDR1 sequence optionally comprises 1, 2, or 3 amino acid exchanges, preferably conservative amino acid exchanges, 1, 2, or 3 amino acid deletions, and/or 1, 2, or 3 amino acid additions:

TABLE 2

Sets of light chain CDR sequences suitable for use in the antibodies or fragments thereof of the present invention
Since the CDR2 light chain sequence of antibody IFX-1 (SEQ ID NO: 12) is identical to the CDR2 light chain sequence of antibody INab708 (SEQ ID NO: 13), sets including SEQ ID NO: 13 would be redundant to sets including SEQ ID NO: 12. Therefore, the table only list four sets of light chain CDR sequences.

| Number of light chain set | CDR3 sequence | CDR2 sequence | CDR1 sequence |
|---|---|---|---|
| I | SEQ ID NO: 8 | SEQ ID NO: 12 | SEQ ID NO: 16 |
| II | SEQ ID NO: 8 | SEQ ID NO: 12 | SEQ ID NO: 17 |
| III | SEQ ID NO: 9 | SEQ ID NO: 12 | SEQ ID NO: 16 |
| IV | SEQ ID NO: 9 | SEQ ID NO: 12 | SEQ ID NO: 17 |

In preferred embodiments of the first, second, third or fourth aspect of the invention, the antibody or antigen-binding fragment thereof comprises one of the heavy CDR sets A-H listed above in Table 1 and one of the light chain CDR sets I-IV listed above in Table 2, i.e. one of the following combinations of sets: A-I, A-II, A-III, A-IV, B-I, B-II, B-IV, C-I, C-II, C-III, C-IV, D-I, D-II, D-IV, E-I, E-II, E-IV, F-I, F-II, F-IV, G-I, G-II, G-IV, H-I, H-II, H-III, or H-IV (wherein the combinations A-I and H-IV are especially preferred),
wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein each heavy chain CDR1 sequence optionally comprises 1, 2, or 3 amino acid exchanges, preferably conservative amino acid exchanges, 1, 2, or 3 amino acid deletions and/or 1, 2, or 3 amino acid additions;
wherein each light chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each light chain CDR1 sequence optionally comprises 1, 2, or 3 amino acid exchanges, preferably conservative amino acid exchanges, 1, 2, or 3 amino acid deletions and/or 1, 2, or 3 amino acid additions.

In preferred embodiments of the first, second, third or fourth aspect of the invention, the antibody or antigen-binding fragment thereof comprises a VH domain that comprises, essentially consists of or consists of (i) the VH domain of IFX-1 or (ii) the VH domain of INab708.

The FR1, CDR1, FR2, CDR2, FR3, CDR3, and FR4 sequences defining the VH domains of IFX-1 and INab708 are shown below in Table 3.

In preferred embodiments of the first, second, third or fourth aspect of the invention, the antibody or antigen-binding fragment thereof comprises a VL domain that comprises, essentially consists of or consists of (i) the VL domain of IFX-1 or (ii) the VL domain of INab708.

The FR1, CDR1, FR2, CDR2, FR3, CDR3, and FR4 sequences defining the VL domains of IFX-1 and INab708 are shown below in Table 3.

TABLE 3

CDR and FR sequences of antibodies IFX-1 and INab708 (Chothia classification mode)

| IFX-1: | INab708: |
|---|---|
| Heavy Chain: | Heavy Chain: |
| FR1: QVQLQQSGPQLVRPGTSVKIS (= SEQ ID NO: 18) | FR1: VQLLESGAELMKPGASVKIS (SEQ ID NO: 26) |
| CDR1: CKASGYSFTTFWMD (= SEQ ID NO: 14) | CDR1: CKATGNTFSGYWIE (= SEQ ID NO: 15) |
| FR2: WVKQRPGQGLEWIGR (SEQ ID NO: 19) | FR2: WVKQRPGHGLEWIGE (SEQ ID NO: 27) |

TABLE 3-continued

CDR and FR sequences of antibodies IFX-1 and INab708 (Chothia classification mode)

| IFX-1: | INab708: |
|---|---|
| CDR2: IDPSDSESRLDQ (= SEQ ID NO: 10) | CDR2: ILPGSGSTNYNE (= SEQ ID NO: 11) |
| FR3: RFKDRATLTVDKSSSTVYMQLSSPTSEDSAVYY (SEQ ID NO: 20) | FR3: KFKGKATLTADTSSNTAYMQLSSLTSEDSAVYY (SEQ ID NO: 28) |
| CDR3: CARGNDGYYGFAY (= SEQ ID NO: 6) | CDR3: CTRRGLYDGSSYFAY (= SEQ ID NO: 7) |
| FR4: WGQGTLVTVSS (SEQ ID NO: 21) | FR4: WGQGTLVTVSA (SEQ ID NO: 29) |
| Light chain: | Light Chain: |
| FR1: DIVLTQSPASLAVSLGQRATIS (SEQ ID NO: 22) | FR1: DIVLTQSPASLAVSLGQRATIS (SEQ ID NO: 30) |
| CDR1: CKASQSVDYDGDSYMK (= SEQ ID NO: 16) | CDR1: CKASQSVDYDGDSYMN (= SEQ ID NO: 17) |
| FR2: WYQQKPGQPPKLL (SEQ ID NO: 23) | FR2: WYQQKPGQPPKLL (SEQ ID NO: 31) |
| CDR2: IYAASNL (= SEQ ID NO: 12) | CDR2: IYAASNL (= SEQ ID NO: 13) |
| FR3: QSGIPARFSGSGSGTDFTLNIHPVEEEDAATYY (SEQ ID NO: 24) | FR3: GSGIPARFSGSGSGTDFTLNIHPVEEEVAATYY (SEQ ID NO: 32) |
| CDR3: CQQSNEDPYT (= SEQ ID NO: 8) | CDR3: CQQNNEDPLT (= SEQ ID NO: 9) |
| FR4: FGGGTKLEIK (SEQ ID NO: 25) | FR4: FGAGTLLELK (SEQ ID NO: 33) |

As will be further explained below in the section "Examples", IFX-1 is a chimeric human/mouse monoclonal IgG4 antibody developed by InflaRx GmbH, Germany. IFX-1 is derived from mouse monoclonal antibody INab308 described in WO 2011/063980 A1. IFX-1 has the same heavy chain variable region and the same light chain variable region as INab308. INab708 is a mouse monoclonal antibody targeting essentially the same conformational epitope as INab308 and IFX-1 and is also described in WO 2011/063980 A1.

In further preferred embodiments of the first, second, third or fourth aspect of the invention, the antibody or antigen-binding fragment thereof comprises a VH domain and a VL domain, wherein (i) said VH domain comprises, essentially consists of or consists of the VH domain of IFX-1 and said VL domain comprises, essentially consists of or consists of the VL domain of IFX-1; or (ii) said VH domain comprises, essentially consists of or consists of the VH domain of INab708 and said VL domain comprises, essentially consists of or consists of the VL domain of INab708.

In preferred embodiments of the first, second, third or fourth aspect of the invention, the antibody or antigen-binding fragment thereof comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

In some embodiments of the first, second, third or fourth aspect of the invention, the binding moiety is an oligonucleotide. In these embodiments, it is further preferred that the oligonucleotide is a nucleic acid aptamer, such as a DNA aptamer or RNA aptamer or a mixed aptamer comprising DNA and RNA nucleotides. In some embodiments, one or more nucleotides may be replaced by modified nucleotides such as 2'-fluorine-substituted pyrimidines. Nucleic acid aptamers may also be conjugated with fluorescent reporter molecules, affinity tags and/or macromolecules. For example, conjugating the aptamer to polyethylenglycol (PEG) or to a comparable macromolecule will increase the biological half-life of the aptamer.

In some embodiments of the first, second, third or fourth aspect of the invention, the binding moiety is an antibody-like protein, e.g. an antibody-like protein as exemplified above in the "Definitions" section.

In some embodiments of the first, second, third or fourth aspect of the invention, the binding moiety is a peptidomimetic. Peptidomimetics suitable for practicing the present invention are preferably based on antibody-like proteins as described above.

The teaching given herein with respect to specific nucleic acid and amino acid sequences, e.g. those shown in the sequence listing, is to be construed so as to also relate to modifications of said specific sequences resulting in sequences which are functionally equivalent to said specific sequences, e g amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain effector functions of an antibody. Preferably, a sequence modified with respect to a specific sequence, when it replaces the specific sequence in an antibody retains binding of said antibody to C5a, in particular to the conformational epitope of C5a identified herein, and preferably retains functions of said antibody as described herein, e.g. blocking C5a-induced lysozyme release from human whole blood cells and/or reducing E. coli induced IL-8 production in human whole blood.

It will be appreciated by those skilled in the art that in particular the sequences of the CDR hypervariable and variable regions can be modified without losing the ability to bind C5a. For example, CDR regions will be either identical or highly homologous to the regions specified herein. By "highly homologous" it is contemplated that from 1 to 5, preferably from 1 to 4, such as 1 to 3 or 1 or 2 exchanges, in particular conservative exchanges, deletions, and/or additions may be made in the CDRs. In addition, the hypervariable and variable regions may be modified so that they show substantial homology with the regions specifically disclosed herein.

Furthermore, it may be desired according to the present invention to modify the amino acid sequences described herein, in particular those of human heavy chain constant regions to adapt the sequence to a desired allotype, e.g. an allotype found in the Caucasian population or in the Chinese population.

The present invention further comprises antibodies in which alterations have been made in the Fc region in order to change the functional or pharmacokinetic properties of the antibodies. Such alterations may result in a decrease or increase of C1q binding and CDC or of FcγR binding and ADCC (antibody-dependent cellular cytotoxicity). Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260.

The in vivo half-life of antibodies can be improved by modifying the salvage receptor epitope of the Ig constant domain or an Ig-like constant domain such that the molecule does not comprise an intact $C_H2$ domain or an intact Ig Fc region, cf. U.S. Pat. Nos. 6,121,022 and 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC (antibody-dependent cellular cytotoxicity) of the antibodies in the presence of NK cells, cf. Shield et al. (2002) J. Biol. Chem., 277: 26733-40. Furthermore, modification of galactosylation can be made in order to modify CDC (complement-dependent cytotoxicity).

Alternatively, in another embodiment, mutations can be introduced randomly along all or part of an anti-C5a antibody coding sequence, such as by saturation mutagenesis, and the resulting modified anti-C5a antibodies can be screened for binding activity.

In the practice of any aspect of the present invention, a pharmaceutical composition as described herein or an inhibitor of C5a (e.g. a binding moiety specifically binding to C5a, especially hC5a, as described herein) may be administered to a patient by any route established in the art which provides a sufficient level of the inhibitor of C5a in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent.

Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, a drug, such as the C5a inhibitor described herein, can be delivered in a controlled-release system. For example, the inhibitor may be administered using intravenous infusion, an implantable osmotic pump, a transdermal patch, liposomes, or other modes of administration. In one embodiment, a pump may be used (see Sefton (1987) CRC Crit. Ref. Biomed. Eng. 14: 201-240; Buchwald et al. (1980) Surgery 88:507-516; Saudek et al. (1989) N. Eng. J. Med. 321:574-579). In another embodiment, the compound can be delivered in a vesicle, in particular a liposome (see R. Langer (1990) Science 249: 1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et al. (1985) Science 228:190; During et al. (1989) Ann. Neurol. 25: 351; Howard et al. (1989) J. Neurosurg. 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, Science 249: 1527-1533).

In a specific embodiment, it may be desirable to administer the pharmaceutical compositions or the C5a inhibitors of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and/or treated or the benefit to be achieved in a normal individual, the body mass of the patient, the patient's age, the route of administration, whether administration is acute or chronic, concomitant medications, and other factors well known to affect the efficacy of administered pharmaceutical agents. Thus, the precise dosage should be decided according to the judgment of the practitioner and each patient's circumstances, e.g. depending upon the condition and the immune status of the individual patient, and according to standard clinical techniques.

The following figures and examples are merely illustrative of the present invention and should not be construed to limit the scope of the invention as indicated by the appended claims in any way.

BRIEF DESCRIPTION OF THE FIGURES

FIGS. 1A and 1B: Blocking activity of IFX-1 to human (FIG. 1A) and monkey (FIG. 1B) eC5a was tested in ZAP-CD11b assay. The data are representatives of 3 separate experiments using different donors.

FIG. 1C: IFX-1 concentrations were measured in the plasma samples from the monkeys 0, 1, 3, 5, and 7 days after infection and antibody administration (n=4 for day 0, 1, 3; n=2 for day 5, 7).

FIGS. 2A, 2B and 2C: Quantitative RT-PCR analysis for C3aR (FIG. 2A), C5aR (FIG. 2B) and MASP2 (FIG. 2C)

were performed on 18 (A/H7N9 group) and 6 (mock group) collected samples from all lung lobes at day 3 post-infection. The data presented are the fold-change (Mean±SEM) as compared to mock.

Figure 2A:
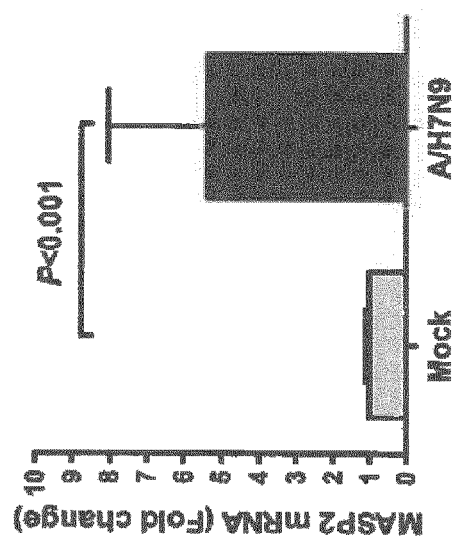
FIGS. 2A-F. Complement activation in AGM lungs after H7N9 virus infection.
Figure 2B:
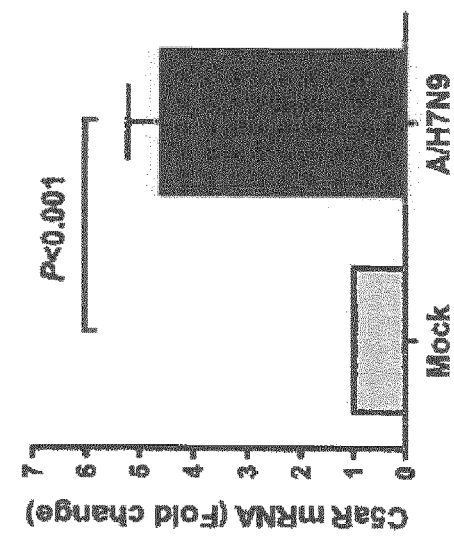
Figure 2C:
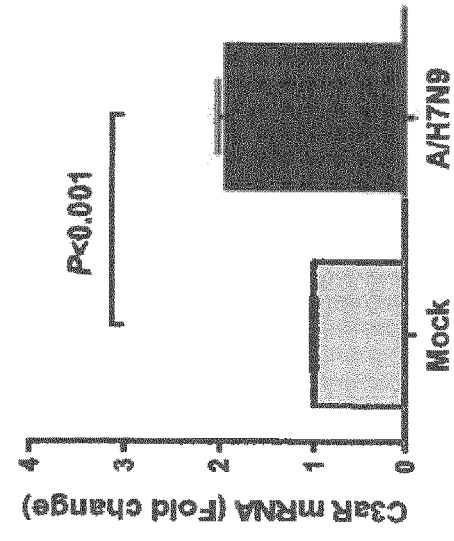
Figure 2D:
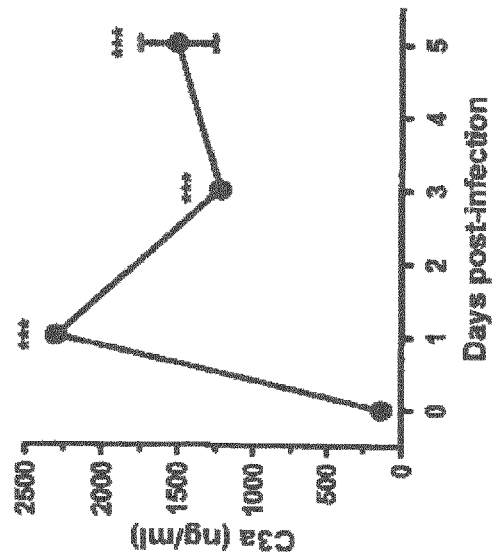
Figure 2E:
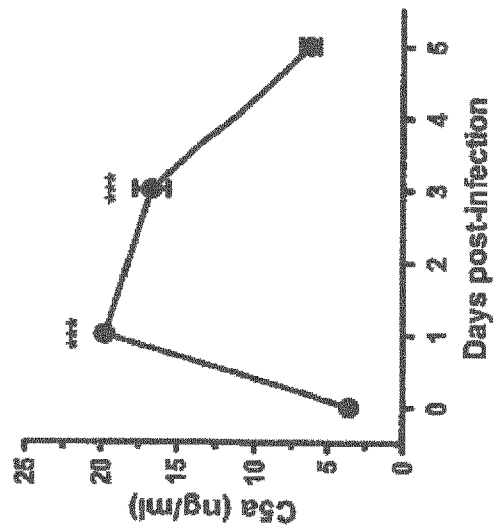
Figure 2F:
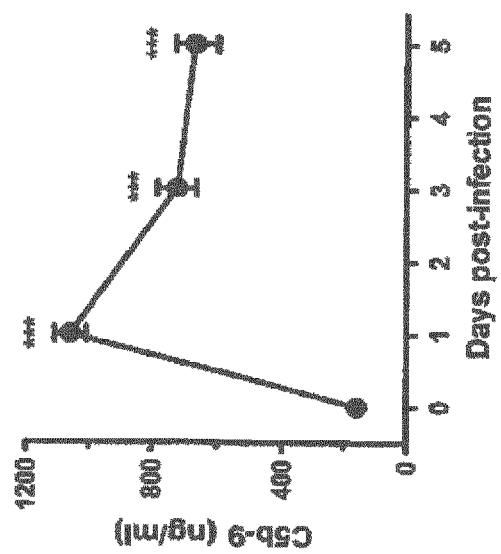

FIGS. 2D, 2E, and 2F: Concentrations of C3a (FIG. 2D), C5a (FIG. 2E) and C5b-9 (FIG. 2F) in A/H7N9-infected AGM plasma were measured by quantitative ELISA. Data are expressed as Mean±SEM on indicated time-point (n=6 at day 0, 1 and 3; n=3 at day 5). *** means P<0.001 vs. day 0.

Figure 3A:
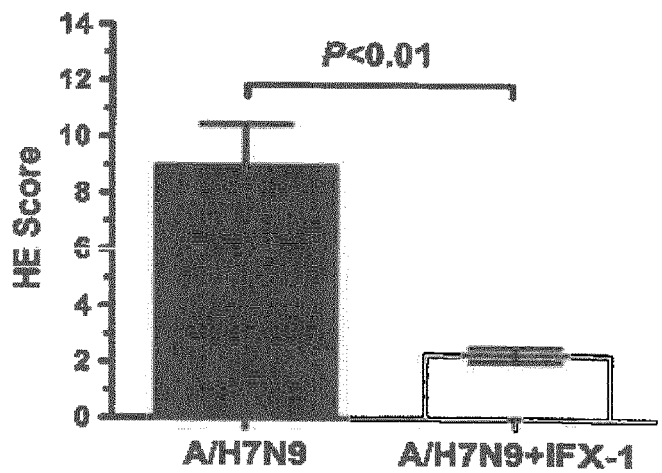
Figure 3B:
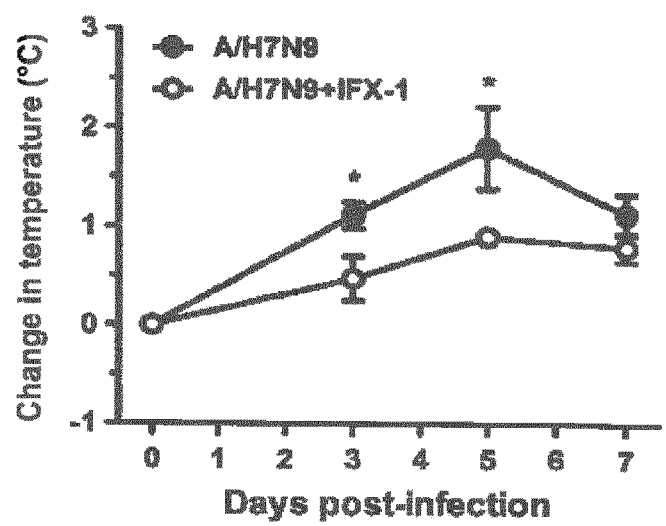
Figure 3C:
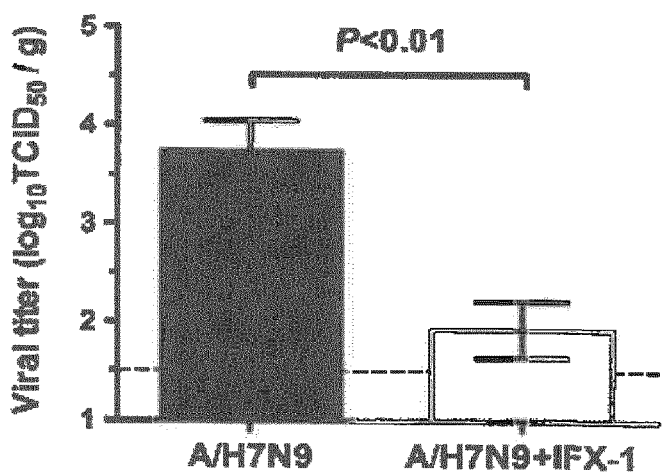

FIGS. 3A-C. Alleviated ALI after A/H7N9 virus infection with anti-C5a antibody treatment.

FIG. 3A: Semiquantitative histopathological analysis at day 3 revealed alleviated lung damages in IFX-1-treated AGMs compared with that of AGMs receiving A/H7N9 infection only (2 AGMs in IFX-1 treated group and 3 AGMs for the control group at each time point).

FIG. 3B: Body temperature change (Mean±SEM) at indicated time-points following A/H7N9 infection. Data shown were calculated by subtracting the temperature measured at day 0 (6 AMGs in A/H7N9 group and 4 AMGs in A/H7N9+ IFX-1 group at day 0 and day 3 post-infection; 3 and 2 AMGs left in respective groups at day 5 and day 7). * means P<0.05 vs A/H7N9 group.

FIG. 3C: Lung viral titer at day 3 post-infection was determined in homogenized samples collected from all lung lobes (n=18 in A/H7N9 group from three AMGs and n=12 in A/H7N9+IFX-1 group from two AMGs). Data were expressed as $TCID_{50}$ per gram of lung tissue (Mean±SEM), and dotted line indicated the limit of detection.

FIGS. 4A-H. Reduced inflammatory responses in AGMs after H7N9 virus infection with anti-C5a antibody treatment.

FIGS. 4A to 4F: Quantitative ELISAs were performed to measure the concentrations of IL-1β (FIG. 4A), IL-6 (FIG. 4B), IP-10 (FIG. 4C), IFN-γ (FIG. 4D), TNF-α (FIG. 4E) and MCP-1 (FIG. 4F) in AGM serum samples. Data presented are concentrations (Mean±SEM) of cytokine and chemokine at indicated time-point, n=6 in A/H7N9 group (solid circle) and n=4 in A/H7N9+IFX-1 group (open circle) at day 0, 1 and 3 post-infection; 3 and 2 AMGs left in respective groups at day 5). * and *** mean P<0.05 and P<0.001 respectively vs. A/H7N9 group.

Figure 4A:
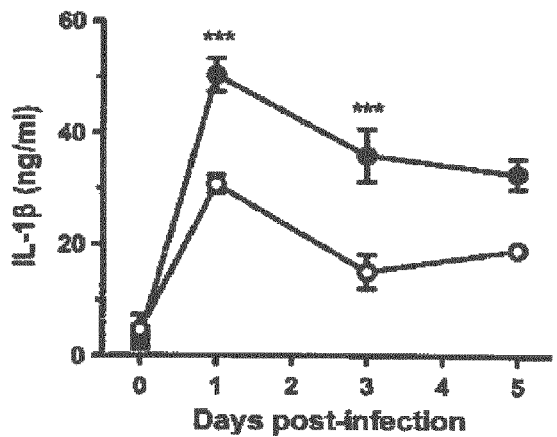
Figure 4B:
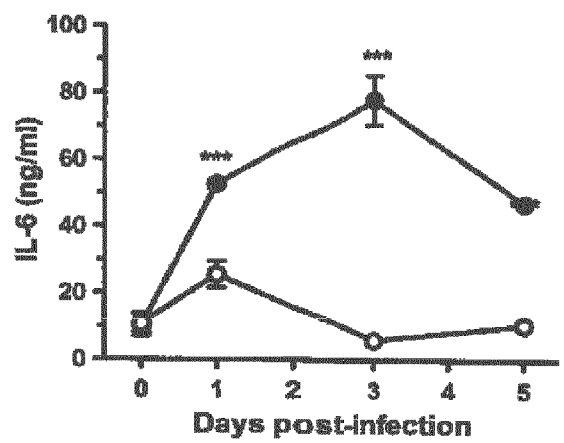
Figure 4C:
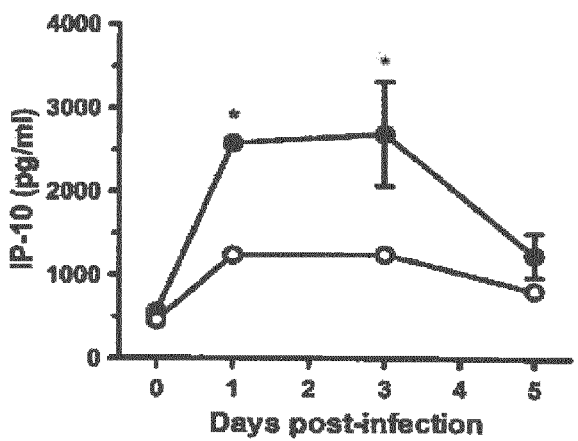
Figure 4D:
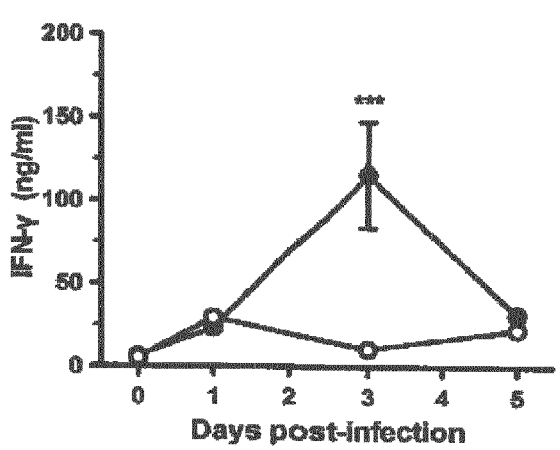
Figure 4E:
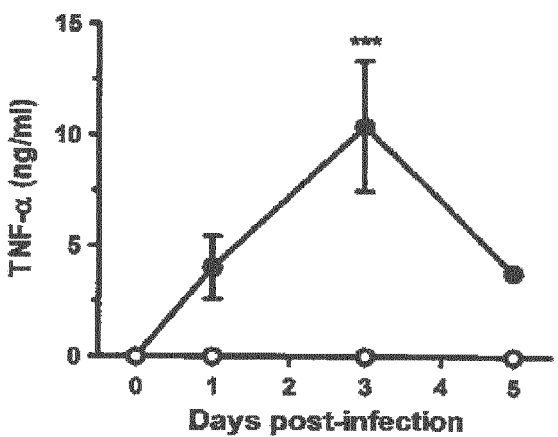
Figure 4F:
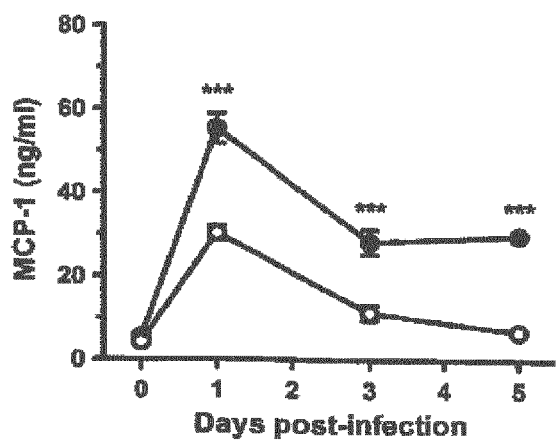
Figure 4G:
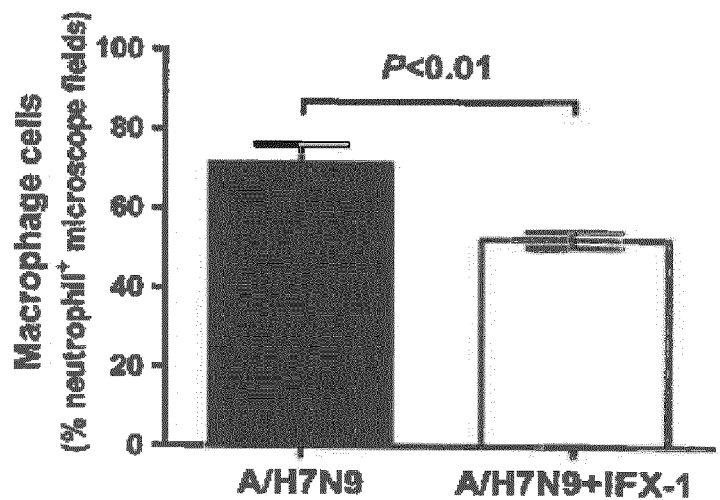
Figure 4H:
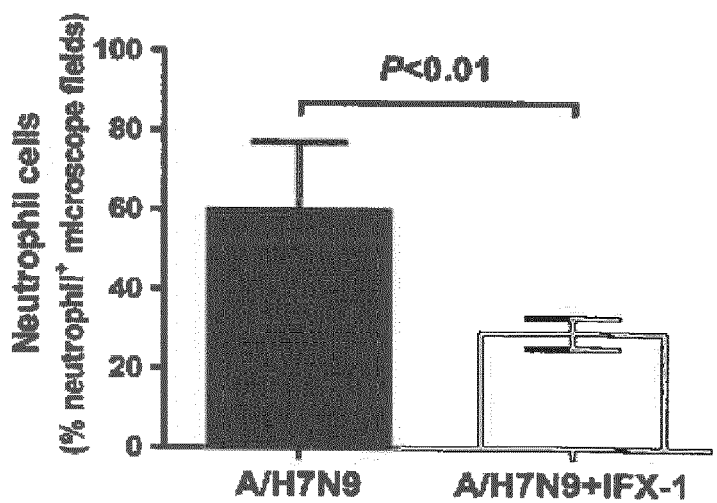

FIGS. 4G and 4H: Semiquantitative analysis of macrophage (FIG. 4G) and neutrophil (FIG. 4H) counts in lungs at day 3 post-infection (n=3 in A/H7N9 group and n=2 in A/H7N9+IFX-1 group).

EXAMPLES

1. Materials and Methods
1.1 Ethics Statement

All procedures involving animals were approved by the Laboratory Animal Center, State Key Laboratory of Pathogen and Biosecurity, Beijing Institute of Microbiology and Epidemiology IACUC's (The permitted number is BIME 2013-15). The study of animals was carried out in strict accordance with the recommendations in the Guide for the Care and Use of Laboratory Animals.

1.2 African Green Monkey Model of H7N9 Virus Infection

Twelve 2-4 years old young adult African Green Monkeys (AGMs) were used in this study, and all the experiments handling live virus and biological samples with a potential contamination of live virus were performed in the biosafety level 3 laboratory. After being anesthetized by intraperitoneal (i.p.) injection of ketamine (5 mg/kg), ten AGMs were inoculated with A/Anhui/1/2013 (H7N9) virus ($10^6 TCID_{50}$) intratracheally and two AGMs were inoculated with the same volume of PBS intratracheally as the negative control. Four of the ten AGMs inoculated with virus were treated with anti-C5a monoclonal antibody (IFX-1; 5 mg/kg) intravenously 30 min after virus inoculation (H7N9+anti-C5a Ab group). Six of the ten AGMs were treated with PBS as control (H7N9+PBS group). The samples from three monkeys in H7N9+PBS group and two monkeys in H7N9+anti-C5a antibody group were collected on days 3 and 7 after infection, respectively. The samples of normal controls were collected on day 3. Heparin plasma and serum were collected on days 0, 1, 3, 5, 7 from all the animals and stored at −70° C. until analysis, and used for evaluating the levels of complement activation products or cytokines.

The animals were euthanized on day 3 after infection by exsanguination under ketamine anesthesia. After being anesthetized, the AGMs' temperature was monitored, and nasal and pharyngeal swabs were taken and placed in 1 ml Dulbecco's modified Eagle's medium supplemented with 100 IU penicillin/ml and 100 μg of streptomycin/ml. The swabs were stored at −70° C. until the $TCID_{50}$ analysis was performed. Necropsies were performed according to a standard protocol. For semiquantitative assessment of gross pathology, the percentage of affected lung tissue at necropsy from each lung lobe was calculated by the area of consolidation and dark red discoloration in each lobe to determine the gross pathology score. For reverse transcription (RT)-PCR, samples were stored in RNA store liquid (Tiangen Biotech Co., Ltd) at 4° C. overnight and then stored at −70° C. until RT-PCR analysis was performed. For histopathology study, the trachea, lung tissues from the cranial, medial, and caudal lobes, liver, spleen, kidney, intestine, brain and lymph nodes were suspended in 10% neutral-buffered formalin overnight and embedded in paraffin, cut at 4 μm and stained with hematoxylin and eosin (H&E) and used for immunohistochemistry.

1.3 Histopathologic Analysis of Lung Damage

Lungs were collected and sampled in a standard procedure from the cranial, medial, and caudal lobes of the lung. Sections of 4 μm thickness were stained with hematoxylin and eosin (H&E) and examined by light microscopy. Trachea and bronchial lesions were assessed according to the extent of denaturated epithelials and inflammatory cell infiltration in the submucous membrane. The injury of parenchyma was analyzed according to the denaturated epithelials, degeneration and necrosis of alveoli pneumocytes, infiltration of inflammatory cells and expansion of parenchymal wall, hemorrhage and interstitial edema (Sun, S. et al. 2011, Am J Respir Cell Mol Biol; 18:834-842). The cumulative scores of size and severity of degeneration or inflammation provided the total score per animal, and the average was taken as the total score for that group.

1.4 Immunohistochemistry Staining for Macrophages and Neutrophils

Formalin-fixed, paraffin-embedded lung sections were de-paraffinized with xylene and hydrated using graded alcohols. The infiltration of macrophages, neutrophils and T lymphocytes was assessed using the following antibodies: CD68, and Myeloperoxidase (MPO) (Beijing Zhongshan Biotechnology Co., Ltd., China). Antibodies were detected using a standard streptavidin-biotin detection system (Beijing Zhongshan Biotechnology Co., Ltd., Beijing, China) according to the manufacturer's instructions.

For semi-quantitative assessment of macrophage and neutrophil infiltration, 30-50 arbitrarily chosen 40× objective fields of lung parenchyma in each lung section were examined by light microscopy for the presence of macrophages or neutrophils in a blinded fashion. The cumulative scores for each animal were expressed as the number of positive fields per 100 fields (%) (Sun, S. et al. 2013, supra).

1.5 Measurement of IFX-1 Concentrations and CD11b Assay

IFX-1 levels in the monkey plasma samples were measured by the standard enzyme-linked immunosorbent assay (ELISA) provided by InflaRx GmbH, Germany CD11b assay was used to assess the blocking efficiency of IFX-1 in human and monkey. Briefly, human or monkey blood was stimulated with plasma or zymosan-activated plasma (ZAP; containing endogenous C5a-eC5a). Different concentrations of IFX-1 and control human IgG4 antibody (Sigma, WI, USA) were added in the assay to determine the IFX-1 blocking activity without any pre-incubation of antibody and eC5a, and eC5a levels were measured by an ELISA kit provided by InflaRx GmbH, Germany. After stimulation, anti-mouse CD11b:FITC or isotype control mAbs (BD Bioscience, NJ, USA) was added and incubated Immediately after the lysing step of red blood cells, CD11b expression on the gated granulocytes was analyzed by the BD FACSCanto™ II flow cytometer. Mean fluorescence intensity (MFI) of FITC-labeled granulocytes was used to examine the level of CD11b expression.

1.6 Measurement of Inflammatory Cytokines and C3a, C5a, C5b-9 in Plasma

Serum or plasma samples of infected AGMs were collected at indicated times and stored at $-70°$ C. before measurement. Cytokine levels of IL-1$\beta$, IL-6, IFN-$\gamma$, TNF-$\alpha$, MCP-1 and IP-10 were measured using the monkey ELISA kits from U-CyTech biosciences or Uscn life science Inc. C3a and C5b-9 levels were measured using the human ELISA kits from BD biosciences, and C5a ELISA was provided by InflaRx GmbH, Jena, Germany. In brief, 100 µl of diluted AGMs serum or plasma were added to the plate pre-coated with antibody specific for individual AGMs cytokines, MPO, C3a, C5a and C5b-9 and incubated at $4°$ C. overnight. Following a wash, enzyme-linked specific antibodies were added and incubated at $37°$ C. for 1 hour. After washing the plates, substrate solution was added and incubated at $37°$ C. for 30 minutes. Assays were developed using TMB, and the reaction was stopped by adding 1N $H_2SO_4$. The absorbance at 450 nm was measured by an ELISA plate reader (Synergy 2, Bio Tek), and the amount of AGMs cytokines, or C3a, C5a and C5b-9 were determined by the standard curve obtained in the measurement.

1.7 Detection of C3aR mRNA, C5aR mRNA and MASP2 Expression

Total RNA was isolated from lung tissue of the cranial, medial, and caudal lobes of AGMs, and relative quantitative real-time RT-PCR was performed. The relative C3aR, C5aR and mannose-binding protein-associated serine protease 2 (MASP2) expression data were analyzed using the $2^{-\Delta\Delta C_T}$ method (Livak, K. J. & Schmittgen T. D. 2001. Methods 25:402-408).

1.8 Virus Titers in Tissues

Bronchia and six parts of lung tissue samples from cranial, medial, and caudal lobes of the right and left lung respectively in each infected AGMs were harvested at indicated times and homogenized using OMNI BEAD RUPTOR 24 tissue grinders (OMNI International, INC.) in minimal essential medium (MEM) plus antibiotics to achieve 10% (w/v) suspensions. Viral titers in tissues were determined by 50% tissue culture infective dose ($TCID_{50}$) as described (Zhao, G. et al. 2010. Virology Journal, 7:151-156). In brief, monolayers of MDCK cells were inoculated with tenfold serial dilutions of homogenates of AGMs organs in quadruplicate. Two hours after inoculation, supernatants were removed and replaced with MEM plus antibiotics and 2 µg/ml TPCK-trypsin (Sigma). Following 3 days' observation of viral cytopathic effect (CPE), infection of the cells was indicated by hemagglutinating activity using 0.5% turkey erythrocytes. Tissue viral titers were calculated by the Reed and Muench method and expressed as $Log_{10}$ $TCID_{50}$/g of tissues.

1.9 Statistical Analysis

Student's t-test with Welch's correction was used for the comparison of data in RT-PCR analysis, semiquantitative histopathological analysis, lung viral titer detection and semiquantitative analysis of macrophage and neutrophil counts. Data of plasma concentrations of C3a, C5a and C5b-9 and blocking activity of IFX-1 to human eC5a were compared using one-way ANOVA with Dunnett's post-test. Differences in temperature changes and inflammatory cytokines and chemokines between the groups at indicated time-points were compared using two-way ANOVA with Bonferroni post-test. P values lower than 0.05 were considered statistically significant. The data are represented as the mean±s.e.m. All analyses were performed in Graphpad Prism version 5.01.

2. Results 2.1 IFX-1 and its Biological Activities

IFX-1 is a chimeric human/mouse monoclonal IgG4 antibody developed by InflaRx GmbH, Germany. The antibody is an IgG4 kappa antibody produced by CHO (Chinese Hamster Ovary) cell line and consists of murine heavy and kappa light chain variable (VH and VL) regions and human gamma 4 heavy chain and kappa light chain constant regions. As disclosed by InflaRx GmbH, IFX-1 has been tested in a monkey toxicological study and in a human phase I trial, and has demonstrated a good safety profile for further clinical trials.

Figure 1A:
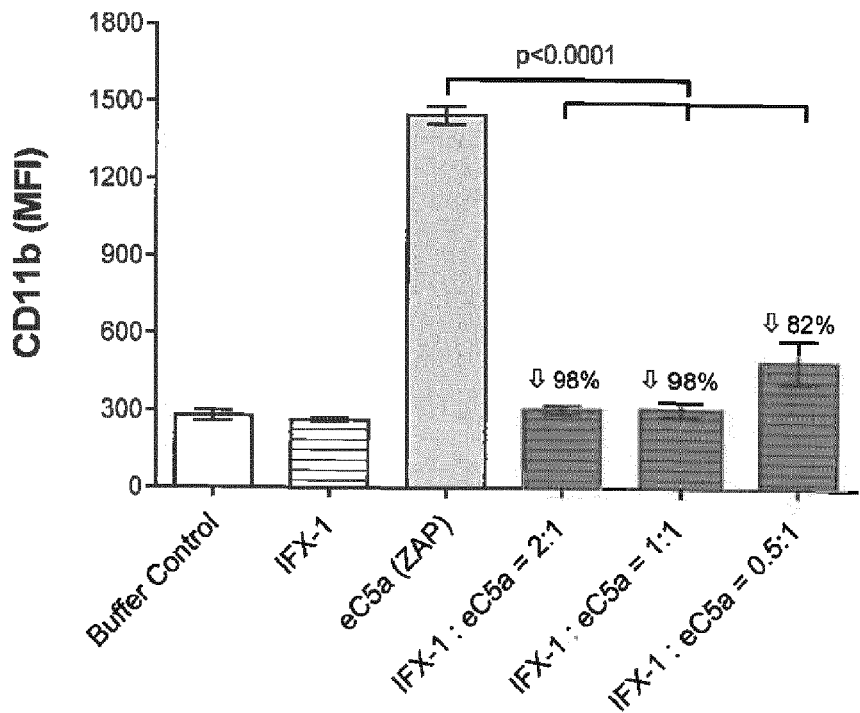
FIGS. 1A-C. IFX-1 biological features.

IFX-1 blocking activity was tested by CD11b assay using endogenous C5a (eC5a) generated from human ZAP samples from 8 different donors. As shown in FIG. 1A, IFX-1 significantly decreased the CD11b expression on human granulocytes by over 80% at an Ab:Ag molar ratio of 0.5:1. The blocking activity of IFX-1 on eC5a-induced CD11b upregulation reached up to 98% when Ab:Ag ratios of 1:1 and 2:1 were applied.

Figure 1B:
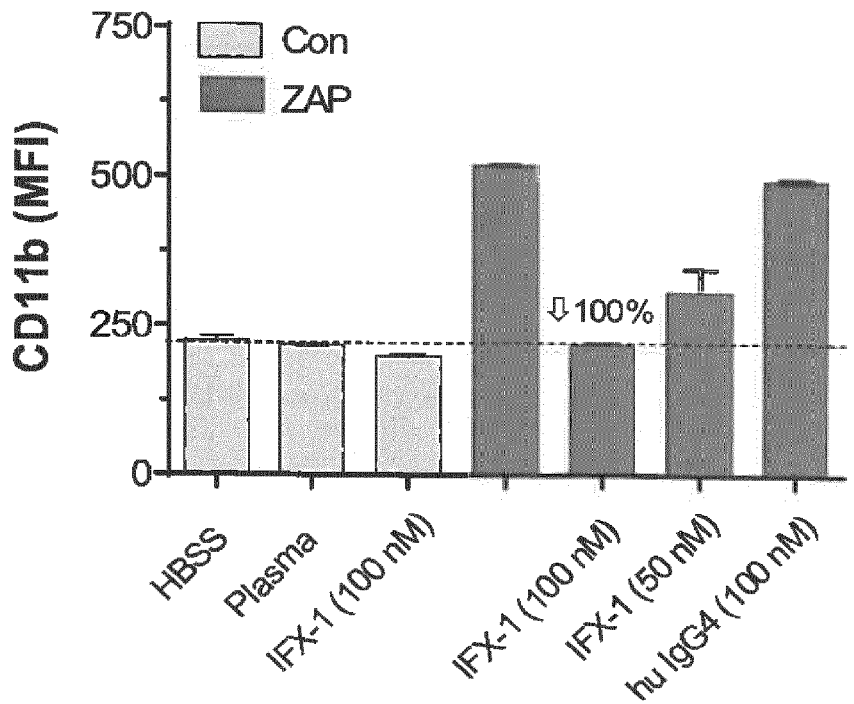

Blocking activity to the monkey C5a was also tested by ZAP-CD11b assay using monkey ZAP and monkey whole blood. IFX-1 is capable of blocking the ZAP-driven CD11b upregulation on monkey granulocytes by 100% (FIG. 1B), indicating that IFX-1 is a fully functional blocking antibody to monkey eC5a.

Figure 1C:
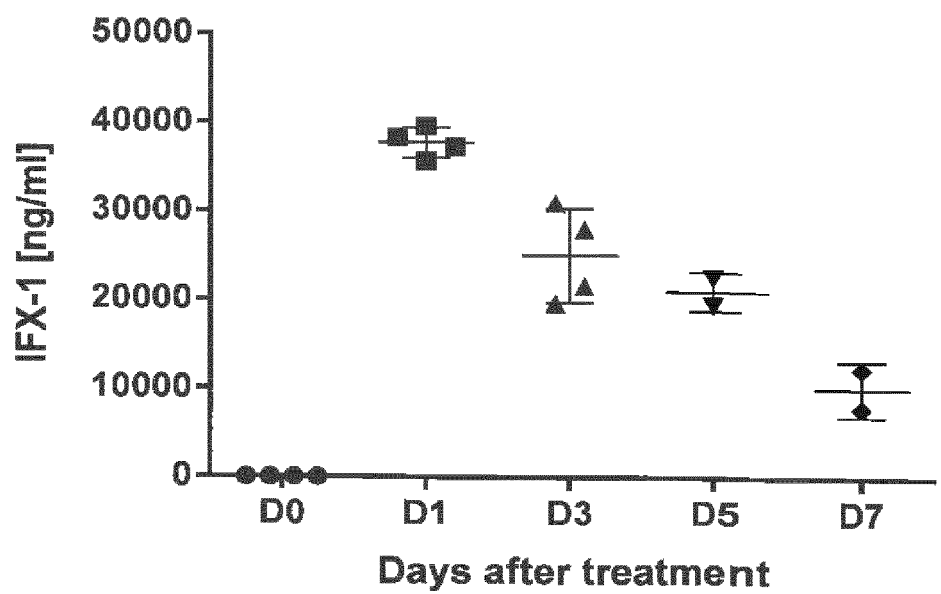

In the monkey model of H7N9 virus infection, a dose of 5 mg/kg of IFX-1 was applied intravenously to treat the four infected monkeys, and its levels were then monitored by the pharmacokinetics assay. There was approximately 40 µg/ml of IFX-1 found in the four treated monkeys 1 day after the treatment, and the level of IFX-1 dropped to around 10 µg/ml in the two monkeys left at day 7 (FIG. 1C). These data indicate that IFX-1 is fully functional to block monkey eC5a and the dose applied for the treatment is sufficient in the model.

2.2 the Pathogenesis of H7N9 Virus-Infected African Green Monkey (AGM)

To explore the pathogenesis of H7N9 virus and the host immune responses to the virus infection, eight AGMs were infected with H7N9 virus (AH1/H7N9), and two AGMs were treated with Mock. Three animals were euthanized on day 3, three further animals were euthanized on day 7 and the remaining two animals were euthanized on day 14 after infection. Lung, trachea, heart, liver, kidney, spleen, brain and intestine were taken from H7N9 virus-infected AGMs and homogenized for virus isolations. Virus can be isolated from lung and trachea but not from other tissue homogenates on day 3 post-infection (Table 4). On day 7 and 14, no virus could be isolated from any of the collected tissues. AGM serum hemagglutination inhibition (HI) titers were detected 7 days after infection, and the HI titers on day 14 were 1:80 to 1:160 (Table 4). Virological and serological tests proved that AGMs were effectively infected by H7N9 virus.

TABLE 4

Tissue virus isolation and serum HI titer.

| | | Group | | | | | | | | | |
|---|---|---|---|---|---|---|---|---|---|---|---|
| | | A/H7N9 Days post-infection | | | | | | | | Mock | |
| | | 3 d | | | 7 d | | | 14 d | | 3 d | 7 d |
| | | AGM Number | | | | | | | | | |
| | | 1 | 2 | 3 | 4 | 5 | 6 | 7 | 8 | 1 | 2 |
| Virus isolation | Lung | + | + | + | − | − | − | − | − | − | − |
| | Trachea | + | + | + | − | − | − | − | − | − | − |
| | Heart | − | − | − | − | − | − | − | − | − | − |
| | Liver | − | − | − | − | − | − | − | − | − | − |
| | Kidney | − | − | − | − | − | − | − | − | − | − |
| | Spleen | − | − | − | − | − | − | − | − | − | − |
| | Brain | − | − | − | − | − | − | − | − | − | − |
| | Intestine | − | − | − | − | − | − | − | − | − | − |
| Serum HI titers | | <1:10 | <1:10 | <1:10 | 1:10 | 1:20 | 1:20 | 1:80 | 1:160 | <1:10 | <1:10 |

On further microscopic observation (data not shown), the peak damage of lung was observed on day 3 after H7N9 virus infection and recovered gradually afterwards. On day 3, when compared with the control group, which was inoculated with PBS, a multifocal trachea-brochoadenitis was observed in the infected lungs, and it was characterized by the denaturated epithelials and moderate infiltration of lymphocytes, macrophages, neutrophils and occasional eosinophils in the submucous membrane of the trachea. The lesions found in the lung infected with H7N9 virus were acute exudative diffuse pulmonary damage which was characterized by denaturated and collapsed epithelials in bronchioles and terminal bronchioles, diffused and thickened alveolar septa with infiltration of lymphocytes, macrophage and neutrophils, denaturated and collapsed pneumocytes, and multifocal hemorrhage in lung interstitial, exudates and severe edema. The endothelial were denaturated with a large number of inflammatory cells adherence and damaged basement membrane. The ultrastructure observation showed degenerated pulmonary epithelial cells with swelling mitochondrial and denatured endoplasmic reticulum, damaged blood-gas barrier with cell debris falling off to alveolar space and inflammatory cells infiltration in the interstitial edema (data not shown).

Among all the other organs examined, including brain, heart, intestine, spleen and kidney, spleen was the only organ showing a certain level of histopathological changes after H7N9 viral infection with a modest elevated number of phagocytes in red pulp and artery cuff of spleen as well as hyperemia and focal haemorrhage in red pulp (data not shown). There was no injury found in other organs such as brain, intestine and kidney.

2.3 Complement Activation in Lung after H7N9 Virus Infection

Although complement activation plays a pivotal role in defense against pathogen invasion, accumulated studies demonstrated that excessive complement activation was associated with a variety of autoimmune and inflammatory diseases (Klos, A. et al. 2009, supra). In this study, the real-time RT-PCR analysis revealed that the transcriptional levels of C3aR, C5aR and MASP2 expression were significantly upregulated at day 1 of H7N9 virus infection (FIGS. 2A, B and C). In addition, the major complement activation product C3a, C5a and C5b-9 levels in plasma samples from AGMs were markedly elevated after H7N9 virus infection. C3a and C5b-9 maintained the high levels at all time-points from 1 to 5 days, while the C5a level was significantly increased at day 1 and day 3 and returned close to the background level at day 5 (FIGS. 2D, E and F). Furthermore, the enhanced protein expression of C3aR and C5aR in lung sections especially in the bronchiole epithelials and the tissues with severe inflammation were demonstrated by immunohistochemistry staining after H7N9 virus infection (data not shown). C3c staining, another indicator of complement activation, also showed an increased deposition in AGM lungs 3 day after H7N9 virus infection (data not shown). These data indicated that the complement system is extensively activated in the circulation as well as in the lungs after H7N9 infection.

2.4 Anti-C5a Antibody Treatment Alleviated the Clinical Signs of ALI Induced by H7N9 Virus Infection To investigate the role of complement activation in the pathogenesis of H7N9 virus infection induced-lung injury, anti-C5a antibody IFX-1 (5 mg/kg) was intravenously injected in the infected AGMs immediately after virus infection. Gross pathology revealed that the infected lungs of AGMs presented multifocal consolidation and dark red discoloration which was most prevalent on the dorsal surface of lungs, while the lungs from the infected AGMs treated with anti-C5a presented almost normal appearance with very little dark red discoloration (data not shown). Histopathological analysis demonstrated that all the infected AGMs developed some degree of pulmonary damage with mild or multifocal bronchointerstitial pneumonia. However, the lung pathology is clearly improved in the lungs from infected AGMs with anti-C5a treatment. On day 3 after infection, the untreated AGMs showed large and multifocal lung lesions with desquamation of bronchiolar epithelial cells, degeneration and necrosis of alveolar epithelial, abundant interstitial edema, multifocal hemorrhage and strong inflammatory infiltration, while mild to moderate expansion of parenchymal wall with less interstitial edema, a much lower number of inflammatory cell infiltrates and a clearly lower degree of lung damage are presented in the infected AGMs with anti-C5a treatment (data not shown). Although the lung injury appeared to be lighter on day 7 than that on day 3 in both the treated and nontreated groups, the degeneration of bronchiolar epithelial cells and pneumocytes, the edema of interstitial especially around the blood vessels were more severe in untreated AGMs than those in treated AGMs on day 7 (data not shown). The semiquantitative histological analysis for the AGM lungs obtained 3 days after infection indicated that the lung histopathologic injury score was greatly attenuated by IFX-1 treatment (FIG. 3A).

The AGMs treated with IFX-1 antibody showed a smaller body temperature fluctuation after H7N9 virus infection when compared to that of non-treated AGMs (FIG. 3B). Surprisingly, the results of viral titers in homogenized lung tissues showed that the mean lung viral titer in treated AGMs was approximately 1.8 log lower than that in untreated AGMs ($p<0.01$) (FIG. 3C), which indicated that the virus replication was somehow reduced after anti-C5a antibody treatment.

2.5 Anti-C5a Antibody Treatment Reduced Inflammatory Responses Initiated by H7N9 Virus Infection in AGMs To further determine the role of complement activation on inflammatory responses initiated by H7N9 virus infection in AGMs, the inflammatory cytokines and chemokines as well as the infiltration of macrophages and neutrophils were evaluated in H7N9 virus infected AGMs with or without the IFX-1 antibody treatment. As shown in FIGS. 4A-H, all the inflammatory mediators investigated in the study were significantly elevated after infection. IL-1β, IP-10 and MCP-1 reached to the peak expression as early as 1 day after infection, while IL-6, TNF-α and IFN-γ showed the peak expression at day 3, and the levels of all the mediators were declined at day 5. The overall expression levels of these inflammatory mediators appear to be significantly hindered in the anti-C5a treated monkeys.

The infiltration of macrophages and neutrophils was measured by immunohistochemistry staining of CD68 and MPO expression in lung tissue sections of AGMs prepared at day 3 post-infection (data not shown). The data showed that both neutrophils and macrophages increased markedly in the infected lungs and the degree of infiltration had a positive correlation with the lesion of lungs. However, the numbers of inflammatory infiltrates especially neutrophils decreased significantly in the lungs of IFX-1 treated monkeys when compared with the non-treated AGMs (FIG. 4G, H). Collectively, the data confirmed the effective therapeutic effect of anti-C5a treatment on the ALI and systemic inflammation initiated by H7N9 viral infection.

| Sequence Listing Free text Information | |
|---|---|
| SEQ ID NO: 6 | IFX-1 CDR3 heavy chain |
| SEQ ID NO: 7 | INab708 CDR3 heavy chain |
| SEQ ID NO: 8 | IFX-1 CDR3 light chain |
| SEQ ID NO: 9 | INab708 CDR3 light chain |
| SEQ ID NO: 10 | IFX-1 CDR2 heavy chain |
| SEQ ID NO: 11 | INab708 CDR2 heavy chain |
| SEQ ID NO: 12 | IFX-1 CDR2 light chain |
| SEQ ID NO: 13 | INab708 CDR2 light chain |
| SEQ ID NO: 14 | IFX-1 CDR1 heavy chain |
| SEQ ID NO: 15 | INab708 CDR1 heavy chain |
| SEQ ID NO: 16 | IFX-1 CDR1 light chain |
| SEQ ID NO: 17 | INab708 CDR1 light chain |
| SEQ ID NO: 18 | IFX-1 FR1 heavy chain |
| SEQ ID NO: 19 | IFX-1 FR2 heavy chain |
| SEQ ID NO: 20 | IFX-1 FR3 heavy chain |
| SEQ ID NO: 21 | IFX-1 FR4 heavy chain |
| SEQ ID NO: 22 | IFX-1 FR1 light chain |
| SEQ ID NO: 23 | IFX-1 FR2 light chain |
| SEQ ID NO: 24 | IFX-1 FR3 light chain |
| SEQ ID NO: 25 | IFX-1 FR4 light chain |
| SEQ ID NO: 26 | INab708 FR1 heavy chain |
| SEQ ID NO: 27 | INab708 FR2 heavy chain |
| SEQ ID NO: 28 | INab708 FR3 heavy chain |
| SEQ ID NO: 29 | INab708 FR4 heavy chain |
| SEQ ID NO: 30 | INab708 FR1 light chain |
| SEQ ID NO: 31 | INab708 FR2 light chain |
| SEQ ID NO: 32 | INab708 FR3 light chain |
| SEQ ID NO: 33 | INab708 FR4 light chain |

The invention claimed is:

1. A method for the reduction of a viral load in a subject suffering from viral pneumonia, wherein the pneumonia in the subject is caused by an HxNx influenza virus, said method comprising the step of:
administering a therapeutic amount of an inhibitor of C5a to said subject, thereby reducing viral load,
wherein the inhibitor of C5a is a binding moiety specifically binding to human C5a,
wherein said binding moiety is an antibody or antigen-binding fragment thereof that comprises three light chain CDR sequences comprising a light chain CDR3 sequence as set forth in SEQ ID NO: 8, a light chain CDR2 sequence according to SEQ ID NO:12, and a light chain CDR1 sequence according to SEQ ID NO:16; and
wherein said antibody or antigen-binding fragment thereof comprises three heavy chain CDR sequences comprising a heavy chain CDR3 sequence as set forth in SEQ ID NO: 6, a heavy chain CDR2 sequence according to SEQ ID NO: 10, and a heavy chain CDR1 sequence according to SEQ ID NO: 14.

2. The method according to claim 1, wherein the subject is a primate.

3. The method according to claim 1, wherein said binding moiety specifically binds to a conformational epitope formed by amino acid sequences NDETCEQRA (SEQ ID NO: 2) and SHKDMQL (SEQ ID NO: 3) of human C5a, and
wherein the binding moiety binds to at least one amino acid within the amino acid sequence according to SEQ ID NO: 2 and to at least one amino acid within the amino acid sequence according to SEQ ID NO: 3.

4. A method for treatment of viral pneumonia caused by an influenza virus in a subject, said method comprising the step of:
administering a therapeutic amount of an inhibitor of C5a to said subject,
wherein the inhibitor of C5a is a binding moiety specifically binding to human C5a,
wherein said binding moiety is an antibody or antigen-binding fragment thereof that comprises three light chain CDR sequences comprising a light chain CDR3 sequence as set forth in SEQ ID NO: 8, a light chain CDR2 sequence according to SEQ ID NO: 12, and a light chain CDR1 sequence according to SEQ ID NO: 16; and
wherein said antibody or antigen-binding fragment thereof comprises three heavy chain CDR sequences comprising a heavy chain CDR3 sequence as set forth in SEQ ID NO: 6, a heavy chain CDR2 sequence according to SEQ ID NO: 10, and a heavy chain CDR1 sequence according to SEQ ID NO: 14; and
wherein the inhibitor is for use as a monotherapy.

5. The method according to claim 4, wherein the pneumonia in the subject is caused by an HxNx influenza virus.

6. The method according to claim 4, wherein the HxNx influenza virus is selected from the group consisting of H1N1, H1N3, H2N2, H3N2, H5N1, H7N2, H7N3, H7N7, H7N9, H9N2, H10N7, and H10N8.

7. The method according to claim 4, wherein said binding moiety specifically binds to a conformational epitope formed by amino acid sequences NDETCEQRA (SEQ ID NO: 2) and SHKDMQL (SEQ ID NO: 3) of human C5a, and wherein the binding moiety binds to at least one amino acid within the amino acid sequence according to SEQ ID NO: 2 and to at least one amino acid within the amino acid sequence according to SEQ ID NO: 3.

8. A method for treatment of viral pneumonia in a subject, said method comprising the step of:

administering a therapeutic amount of an inhibitor of C5a to said subject, wherein the inhibitor of C5a is a binding moiety specifically binding to human C5a, wherein said binding moiety is an antibody or antigen-binding fragment thereof that comprises three light chain CDR sequences comprising a light chain CDR3 sequence as set forth in SEQ ID NO: 8, a light chain CDR2 sequence according to SEQ ID NO: 12, and a light chain CDR1 sequence according to SEQ ID NO: 16; and wherein said antibody or antigen-biding fragment thereof comprises three heavy chain CDR sequences comprising a heavy chain CDR3 sequence as set forth in SEQ ID NO: 6, a heavy chain CDR2 sequence according to SEQ ID NO: 10, and a heavy chain CDR1 sequence according to SEQ ID NO: 14; and wherein the viral pneumonia in the subject is caused by an H7N9 influenza virus.

9. The method according to claim 8, wherein the subject is a primate.

10. A method for treatment of viral pneumonia caused by an HxNx influenza virus in a subject, said method comprising the step of:

administering a therapeutic amount of an inhibitor of C5a to said subject, wherein the subject is a primate, wherein the inhibitor of C5a is a binding moiety specifically binding to human C5a, wherein said binding moiety is an antibody or antigen-binding fragment thereof that comprises three light chain CDR sequences comprising a light chain CDR3 sequence as set forth in SEQ ID NO: 8, a light chain CDR2 sequence according to SEQ ID NO: 12, and a light chain CDR1 sequence according to SEQ ID NO: 16; and wherein said antibody or antigen-binding fragment thereof comprises three heavy chain CDR sequences comprising a heavy chain CDR3 sequence as set forth in SEQ ID NO: 6, a heavy chain CDR2 sequence according to SEQ ID NO: 10, and a heavy chain CDR1 sequence according to SEQ ID NO: 14.

11. The method according to claim 10, wherein the HxNx influenza virus is selected from the group consisting of H1N1, H1N3, H2N2, H3N2, H5N1, H7N2, H7N3, H7N7, H7N9, H9N2, H10N7, and H10N8.

12. The method according to claim 10, wherein said binding moiety specifically binds to a conformational epitope formed by amino acid sequences NDETCEQRA (SEQ ID NO: 2) and SHKDMQL (SEQ ID NO: 3) of human C5a, and wherein the binding moiety binds to at least one amino acid within the amino acid sequence according to SEQ ID NO: 2 and to at least one amino acid within the amino acid sequence according to SEQ ID NO: 3.

13. The method according to claim 1, wherein the HxNx influenza virus is selected from the group consisting of H1N1, H1N3, H2N2, H3N2, H5N1, H7N2, H7N3, H7N7, H7N9, H9N2, H10N7, and H10N8.

* * * * *

SEQUENCE LISTING

```
<160> NUMBER OF SEQ ID NOS: 33

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 2
```

```
<211> LENGTH: 9
<212> TYPE: PRT
<213> ORGANISM: Homo sapiens

<400> SEQUENCE: 2

Asn Asp Glu Thr Cys Glu Gln Arg Ala
1               5

<210> SEQ ID NO 3
<211> LENGTH: 7
<212> TYPE: PRT
<213> ORGANISM: Homo sapiens

<400> SEQUENCE: 3

Ser His Lys Asp Met Gln Leu
1               5

<210> SEQ ID NO 4
<211> LENGTH: 7
<212> TYPE: PRT
<213> ORGANISM: Homo sapiens

<400> SEQUENCE: 4

Asp Glu Thr Cys Glu Gln Arg
1               5

<210> SEQ ID NO 5
<211> LENGTH: 5
<212> TYPE: PRT
<213> ORGANISM: Homo sapiens

<400> SEQUENCE: 5

His Lys Asp Met Gln
1               5

<210> SEQ ID NO 6
<211> LENGTH: 13
<212> TYPE: PRT
<213> ORGANISM: Artificial Sequence
<220> FEATURE:
<223> OTHER INFORMATION: IFX-1 CDR3 heavy chain

<400> SEQUENCE: 6

Cys Ala Arg Gly Asn Asp Gly Tyr Tyr Gly Phe Ala Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: INab708 CDR3 heavy chain

<400> SEQUENCE: 7

Cys Thr Arg Arg Gly Leu Tyr Asp Gly Ser Ser Tyr Phe Ala Tyr
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: IFX-1 CDR3 light chain

<400> SEQUENCE: 8

Cys Gln Gln Ser Asn Glu Asp Pro Tyr Thr
```

<210> SEQ ID NO 9
<211> LENGTH: 10
<212> TYPE: PRT
<213> ORGANISM: Artificial Sequence
<220> FEATURE:
<223> OTHER INFORMATION: INab708 CDR3 light chain

<400> SEQUENCE: 9

Cys Gln Gln Asn Asn Glu Asp Pro Leu Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: IFX-1 CDR2 heavy chain

<400> SEQUENCE: 10

Ile Asp Pro Ser Asp Ser Glu Ser Arg Leu Asp Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: INab708 CDR2 heavy chain

<400> SEQUENCE: 11

Ile Leu Pro Gly Ser Gly Ser Thr Asn Tyr Asn Glu
1               5                   10

<210> SEQ ID NO 12
<211> LENGTH: 7
<212> TYPE: PRT
<213> ORGANISM: Artificial Sequence
<220> FEATURE:
<223> OTHER INFORMATION: IFX-1 CDR2 light chain

<400> SEQUENCE: 12

Ile Tyr Ala Ala Ser Asn Leu
1               5

<210> SEQ ID NO 13
<211> LENGTH: 7
<212> TYPE: PRT
<213> ORGANISM: Artificial Sequence
<220> FEATURE:
<223> OTHER INFORMATION: INab708 CDR2 light chain

<400> SEQUENCE: 13

Ile Tyr Ala Ala Ser Asn Leu
1               5

<210> SEQ ID NO 14
<211> LENGTH: 14
<212> TYPE: PRT
<213> ORGANISM: Artificial Sequence
<220> FEATURE:
<223> OTHER INFORMATION: IFX-1 CDR1 heavy chain

<400> SEQUENCE: 14

Cys Lys Ala Ser Gly Tyr Ser Phe Thr Thr Phe Trp Met Asp
1               5                   10

<210> SEQ ID NO 15
<211> LENGTH: 14
<212> TYPE: PRT
<213> ORGANISM: Artificial Sequence
<220> FEATURE:
<223> OTHER INFORMATION: INab708 CDR1 heavy chain

<400> SEQUENCE: 15

Cys Lys Ala Thr Gly Asn Thr Phe Ser Gly Tyr Trp Ile Glu
1               5                   10

<210> SEQ ID NO 16
<211> LENGTH: 16
<212> TYPE: PRT
<213> ORGANISM: Artificial Sequence
<220> FEATURE:
<223> OTHER INFORMATION: IFX-1 CDR1 light chain

<400> SEQUENCE: 16

Cys Lys Ala Ser Gln Ser Val Asp Tyr Asp Gly Asp Ser Tyr Met Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: INab708 CDR1 light chain

<400> SEQUENCE: 17

Cys Lys Ala Ser Gln Ser Val Asp Tyr Asp Gly Asp Ser Tyr Met Asn
1               5                   10                  15

<210> SEQ ID NO 18
<211> LENGTH: 21
<212> TYPE: PRT
<213> ORGANISM: Artificial Sequence
<220> FEATURE:
<223> OTHER INFORMATION: IFX-1 FR1 heavy chain

<400> SEQUENCE: 18

Gln Val Gln Leu Gln Gln Ser Gly Pro Gln Leu Val Arg Pro Gly Thr
1               5                   10                  15

Ser Val Lys Ile Ser
            20

<210> SEQ ID NO 19
<211> LENGTH: 15
<212> TYPE: PRT
<213> ORGANISM: Artificial Sequence
<220> FEATURE:
<223> OTHER INFORMATION: IFX-1 FR2 heavy chain

<400> SEQUENCE: 19

Trp Val Lys Gln Arg Pro Gly Gln Gly Leu Glu Trp Ile Gly Arg
1               5                   10                  15

<210> SEQ ID NO 20
<211> LENGTH: 33
<212> TYPE: PRT
<213> ORGANISM: Artificial Sequence
<220> FEATURE:
<223> OTHER INFORMATION: IFX-1 FR3 heavy chain

<400> SEQUENCE: 20

```
Arg Phe Lys Asp Arg Ala Thr Leu Thr Val Asp Lys Ser Ser Ser Thr
1               5                   10                  15

Val Tyr Met Gln Leu Ser Ser Pro Thr Ser Glu Asp Ser Ala Val Tyr
            20                  25                  30

Tyr
```

<210> SEQ ID NO 21
<211> LENGTH: 11
<212> TYPE: PRT
<213> ORGANISM: Artificial Sequence
<220> FEATURE:
<223> OTHER INFORMATION: IFX-1 FR4 heavy chain

<400> SEQUENCE: 21

```
Trp Gly Gln Gly Thr Leu Val Thr Val Ser Ser
1               5                   10
```

<210> SEQ ID NO 22
<211> LENGTH: 22
<212> TYPE: PRT
<213> ORGANISM: Artificial Sequence
<220> FEATURE:
<223> OTHER INFORMATION: IFX-1 FR1 light chain

<400> SEQUENCE: 22

```
Asp Ile Val Leu Thr Gln Ser Pro Ala Ser Leu Ala Val Ser Leu Gly
1               5                   10                  15

Gln Arg Ala Thr Ile Ser
            20
```

<210> SEQ ID NO 23
<211> LENGTH: 13
<212> TYPE: PRT
<213> ORGANISM: Artificial Sequence
<220> FEATURE:
<223> OTHER INFORMATION: IFX-1 FR2 light chain

<400> SEQUENCE: 23

```
Trp Tyr Gln Gln Lys Pro Gly Gln Pro Pro Lys Leu Leu
1               5                   10
```

<210> SEQ ID NO 24
<211> LENGTH: 33
<212> TYPE: PRT
<213> ORGANISM: Artificial Sequence
<220> FEATURE:
<223> OTHER INFORMATION: IFX-1 FR3 light chain

<400> SEQUENCE: 24

```
Gln Ser Gly Ile Pro Ala Arg Phe Ser Gly Ser Gly Ser Gly Thr Asp
1               5                   10                  15

Phe Thr Leu Asn Ile His Pro Val Glu Glu Glu Asp Ala Ala Thr Tyr
            20                  25                  30

Tyr
```

<210> SEQ ID NO 25
<211> LENGTH: 10
<212> TYPE: PRT
<213> ORGANISM: Artificial Sequence
<220> FEATURE:
<223> OTHER INFORMATION: IFX-1 FR4 light chain

<400> SEQUENCE: 25

```
Phe Gly Gly Gly Thr Lys Leu Glu Ile Lys
```

<210> SEQ ID NO 26
<211> LENGTH: 20
<212> TYPE: PRT
<213> ORGANISM: Artificial Sequence
<220> FEATURE:
<223> OTHER INFORMATION: INab708 FR1 heavy chain

<400> SEQUENCE: 26

Val Gln Leu Leu Glu Ser Gly Ala Glu Leu Met Lys Pro Gly Ala Ser
1               5                   10                  15

Val Lys Ile Ser
            20

<210> SEQ ID NO 27
<211> LENGTH: 15
<212> TYPE: PRT
<213> ORGANISM: Artificial Sequence
<220> FEATURE:
<223> OTHER INFORMATION: INab708 FR2 heavy chain

<400> SEQUENCE: 27

Trp Val Lys Gln Arg Pro Gly His Gly Leu Glu Trp Ile Gly Glu
1               5                   10                  15

<210> SEQ ID NO 28
<211> LENGTH: 33
<212> TYPE: PRT
<213> ORGANISM: Artificial Sequence
<220> FEATURE:
<223> OTHER INFORMATION: INab708 FR3 heavy chain

<400> SEQUENCE: 28

Lys Phe Lys Gly Lys Ala Thr Leu Thr Ala Asp Thr Ser Ser Asn Thr
1               5                   10                  15

Ala Tyr Met Gln Leu Ser Ser Leu Thr Ser Glu Asp Ser Ala Val Tyr
                20                  25                  30

Tyr

<210> SEQ ID NO 29
<211> LENGTH: 11
<212> TYPE: PRT
<213> ORGANISM: Artificial Sequence
<220> FEATURE:
<223> OTHER INFORMATION: INab708 FR4 heavy chain

<400> SEQUENCE: 29

Trp Gly Gln Gly Thr Leu Val Thr Val Ser Ala
1               5                   10

<210> SEQ ID NO 30
<211> LENGTH: 22
<212> TYPE: PRT
<213> ORGANISM: Artificial Sequence
<220> FEATURE:
<223> OTHER INFORMATION: INab708 FR1 light chain

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser
            20

```
<210> SEQ ID NO 31
<211> LENGTH: 13
<212> TYPE: PRT
<213> ORGANISM: Artificial Sequence
<220> FEATURE:
<223> OTHER INFORMATION: INab708 FR2 light chain

<400> SEQUENCE: 31

Trp Tyr Gln Gln Lys Pro Gly Gln Pro Pro Lys Leu Leu
1               5                   10

<210> SEQ ID NO 32
<211> LENGTH: 33
<212> TYPE: PRT
<213> ORGANISM: Artificial Sequence
<220> FEATURE:
<223> OTHER INFORMATION: INab708 FR3 light chain

<400> SEQUENCE: 32

Gly Ser Gly Ile Pro Ala Arg Phe Ser Gly Ser Gly Ser Gly Thr Asp
1               5                   10                  15

Phe Thr Leu Asn Ile His Pro Val Glu Glu Val Ala Ala Thr Tyr
            20                  25                  30

Tyr

<210> SEQ ID NO 33
<211> LENGTH: 10
<212> TYPE: PRT
<213> ORGANISM: Artificial Sequence
<220> FEATURE:
<223> OTHER INFORMATION: INab708 FR4 light chain

<400> SEQUENCE: 33

Phe Gly Ala Gly Thr Leu Leu Glu Leu Lys
1               5                   10
```